(12) United States Patent
Fukasawa et al.

(10) Patent No.: US 9,975,099 B2
(45) Date of Patent: May 22, 2018

(54) FUEL SYNTHESIS CATALYST AND FUEL SYNTHESIS SYSTEM

(71) Applicant: Kabushiki Kaisha Toshiba, Minato-ku (JP)

(72) Inventors: Takayuki Fukasawa, Yokohama (JP); Kenji Essaki, Kawasaki (JP); Shinsuke Matsuno, Minato (JP); Takashi Kuboki, Ota (JP); Yasuhiro Goto, Minato (JP); Seiichi Suenaga, Yokohama (JP)

(73) Assignee: Kabushiki Kaisha Toshiba, Minato-ku (JP)

(*) Notice: Subject to any disclaimer, the term of this patent is extended or adjusted under 35 U.S.C. 154(b) by 0 days. days.

(21) Appl. No.: 15/457,449

(22) Filed: Mar. 13, 2017

(65) Prior Publication Data

US 2017/0266636 A1 Sep. 21, 2017

Related U.S. Application Data

(63) Continuation-in-part of application No. 15/255,741, filed on Sep. 2, 2016.

(30) Foreign Application Priority Data

Mar. 16, 2016 (JP) .................................. 2016-053111
Feb. 28, 2017 (JP) .................................. 2017-036344

(51) Int. Cl.
*B01J 35/02* (2006.01)
*B01J 8/06* (2006.01)
(Continued)

(52) U.S. Cl.
CPC .............. *B01J 8/065* (2013.01); *B01J 21/04* (2013.01); *B01J 21/063* (2013.01); *B01J 21/08* (2013.01);
(Continued)

(58) Field of Classification Search
CPC . C10G 2/50; C10G 2/332; C10G 2/341; B01J 35/008; B01J 35/023; B01J 35/0006; B01J 8/065; C07C 29/156; C07C 1/0435
See application file for complete search history.

(56) References Cited

U.S. PATENT DOCUMENTS 4,032,556 A 6/1977 Banks
4,242,103 A 12/1980 Rabo et al.
(Continued)

FOREIGN PATENT DOCUMENTS

EP 0 225 953 A1 6/1987
JP 60-132649 A 7/1985
(Continued)

OTHER PUBLICATIONS

Shohei Tada et al. "Ni/CeO$_2$ catalysts with high CO$_2$ methanation activity and high CH$_4$ selectivity at low temperatures", International Journal of Hydrogen Energy 37, 2012, 5 pages.

*Primary Examiner* — Lessanework Seifu
(74) *Attorney, Agent, or Firm* — Oblon, McClelland, Maier & Neustadt, L.L.P.

(57) ABSTRACT

A fuel synthesis catalyst of an embodiment for hydrogenating a gas includes at least one selected from the group consisting of; carbon dioxide and carbon monoxide, the catalyst comprising, a base material containing at least one oxide selected from the group consisting of; Al$_2$O$_3$, MgO, TiO$_2$, and SiO$_2$, first metals containing at least one metal selected from the group consisting of; Ni, Co, Fe, and Cu and brought into contact with the base material, and a first oxide containing at least one selected from the group consisting of; CeO$_2$, ZrO$_2$, TiO$_2$, and SiO$_2$ and having an interface with each of the first metals and the base material. The first metals exist on an outer surface of the base material, and on a surface of the base material in fine pores having opening ends on the outer surface of the base
(Continued)

material and inside the base material. The first metals and the first oxide exist in the fine pores. The first metals have interfaces with the base material in the fine pores. The first metals exist inside the base material.

20 Claims, 12 Drawing Sheets

(51) Int. Cl.

| | | |
|---|---|---|
| *C07C 29/156* | (2006.01) | |
| *C10G 2/00* | (2006.01) | |
| *B01J 23/755* | (2006.01) | |
| *B01J 21/04* | (2006.01) | |
| *B01J 23/83* | (2006.01) | |
| *B01J 23/02* | (2006.01) | |
| *B01J 21/06* | (2006.01) | |
| *B01J 21/08* | (2006.01) | |
| *B01J 35/00* | (2006.01) | |
| *B01J 37/02* | (2006.01) | |
| *B01J 37/08* | (2006.01) | |

(52) U.S. Cl.
CPC ............ *B01J 23/02* (2013.01); *B01J 23/755* (2013.01); *B01J 23/83* (2013.01); *B01J 35/0006* (2013.01); *B01J 35/026* (2013.01); *B01J 37/024* (2013.01); *B01J 37/0236* (2013.01); *B01J 37/088* (2013.01); *C07C 29/156* (2013.01); *C10G 2/332* (2013.01); *C10G 2/34* (2013.01); *C10G 2/50* (2013.01); *B01J 2208/024* (2013.01); *B01J 2208/06* (2013.01)

(56) References Cited

U.S. PATENT DOCUMENTS

| | | |
|---|---|---|
| 4,605,676 A | 8/1986 | Kobylinkski et al. |
| 6,638,889 B1 | 10/2003 | Van Berge et al. |
| 2007/0099797 A1 | 5/2007 | Hu et al. |
| 2015/0246347 A1 | 9/2015 | Miyao et al. |
| 2015/0360209 A1 | 12/2015 | Teunissen et al. |
| 2017/0001168 A1 | 1/2017 | Park et al. |

FOREIGN PATENT DOCUMENTS

| | | |
|---|---|---|
| JP | 62-140652 | 6/1987 |
| JP | 63-039634 A | 2/1988 |
| JP | 63-24979 | 5/1988 |
| JP | 2002-503546 A | 2/2002 |
| JP | 2004-528176 A | 9/2004 |
| JP | 2007-252990 A | 10/2007 |
| JP | 2008-155147 A | 7/2008 |
| JP | 2008-155181 A | 7/2008 |
| JP | 2009-34650 | 2/2009 |
| JP | 2010-44966 | 2/2010 |
| JP | 2012-187485 | 10/2012 |
| JP | 5094028 | 12/2012 |
| WO | 2014/038426 A1 | 3/2014 |

US 9,975,099 B2

FUEL SYNTHESIS CATALYST AND FUEL SYNTHESIS SYSTEM

CROSS-REFERENCE TO RELATED APPLICATION

This is a Continuation-in-Part application of U.S. patent application Ser. No. 15/255,741, filed Sep. 2, 2016, the entire contents of which are incorporated herein by reference.

This application is based upon and claims the benefit of priority from Japanese Patent Applications No. 2016-53111, filed on Mar. 16, 2016 and No 2017-036344 filed on Feb. 28, 2017; the entire contents of which are incorporated herein by reference.

FIELD

Embodiments described herein relate to a fuel synthesis catalyst and a fuel synthesis system.

BACKGROUND

In recent years, renewable energy of sunlight, wind power, or the like has attracted attention as safe and clean energy, and an increase in introduction quantity thereof is expected in the future. However, such renewable energy has a low operation rate and a large output fluctuation in a short time, and has a problem in terms of stable supply. Further, if a large quantity of such renewable energy is introduced, a problem arises in that the introduced energy is not completely consumed and remains as surplus power. In this regard, there is a demand for development of techniques of storing electric power such that electric power can be stably supplied and only a necessary amount of electric power can be supplied whenever it is needed even if the introduction of such renewable energy increases. For storing electric power, in addition to a method of storing electric power in the form of electricity, a method of converting electric power into chemical energy and storing the chemical energy has been investigated. In particular, the method of storing electric power in the form of chemical energy has advantages in that the chemical power can be stored in the unit of several days to weeks or a longer span and the chemical power can be transported and used at a different place as necessary. Recently, a method of storing the electric power in the form of hydrogen attracts attention; however, methane or methanol, which is excellent in volumetric energy density as compared with hydrogen, is also a major candidate. In particular, regarding methane or the like, there are a plenty of devices capable of directly using methane or the like as a fuel and the infrastructure therefor is also established.

For example, reaction (1) in which methane is synthesized from hydrogen ($H_2$) obtainable by electrolyzing water by renewable energy and carbon dioxide ($CO_2$) and reaction (2) in which methanol is synthesized from hydrogen ($H_2$) and carbon monoxide (CO) are mentioned.

$$CO_2 + 4H_2 \rightarrow CH_4 + 2H_2O \qquad (1)$$

$$CO + 2H_2 \rightarrow CH_3OH \qquad (2)$$

This reaction (1) called Sabatier reaction is a reaction for reductive regeneration of $CO_2$ that is one of causes of global warming, and since the reaction is performed at a relatively low temperature of about 400° C., a great deal of research has hitherto been conducted on this reaction.

According to this reaction, the conversion of $CO_2$ and the yield of methane can be increased as the reaction approaches equilibrium and a lower temperature region; however, the reaction rate is decreased, and thus, it is more difficult to put this reaction into practical use. For this reason, when the reaction is carried out at low temperature, a noble metal-based catalyst is necessary. However, the noble metal-based catalyst is expensive. Meanwhile, when the temperature is increased to about 400° C., the reaction rate is increased and a Ni-based catalyst can be used. However, in this case, a by-product such as CO is also generated, and as a result, energy is consumed for separation of the by-product, or the like. In this regard, there is a demand for development of a non-noble metal-based catalyst having high activity at a lower temperature region and high methane yield.

As a catalyst having high activity at low temperature of the related art, for example, a Ni-based catalyst having $ZrO_2$ or $CeO_2$ as a base material has been known. It is known that a Ni catalyst supported on a $CeO_2$ base material has high reaction activity at low temperature. It is considered that these base materials have oxygen defects and help CO or $CO_2$ to be easily dissociated at lower temperature and cause the reaction with hydrogen at low temperature to be performed effectively.

However, these catalysts have metal particles supported on a base material that is powder and thus are difficult to handle without any change, and it is necessary to granulate these catalysts in a suitable size using a binder or the like. Further, there is also a problem in durability such as weak binding force between the metal particles and the base material. In particular, since methanation reaction is exothermic reaction, heat resistance to withstand a local temperature increase is also required.

DETAILED DESCRIPTION

Figure 1A:
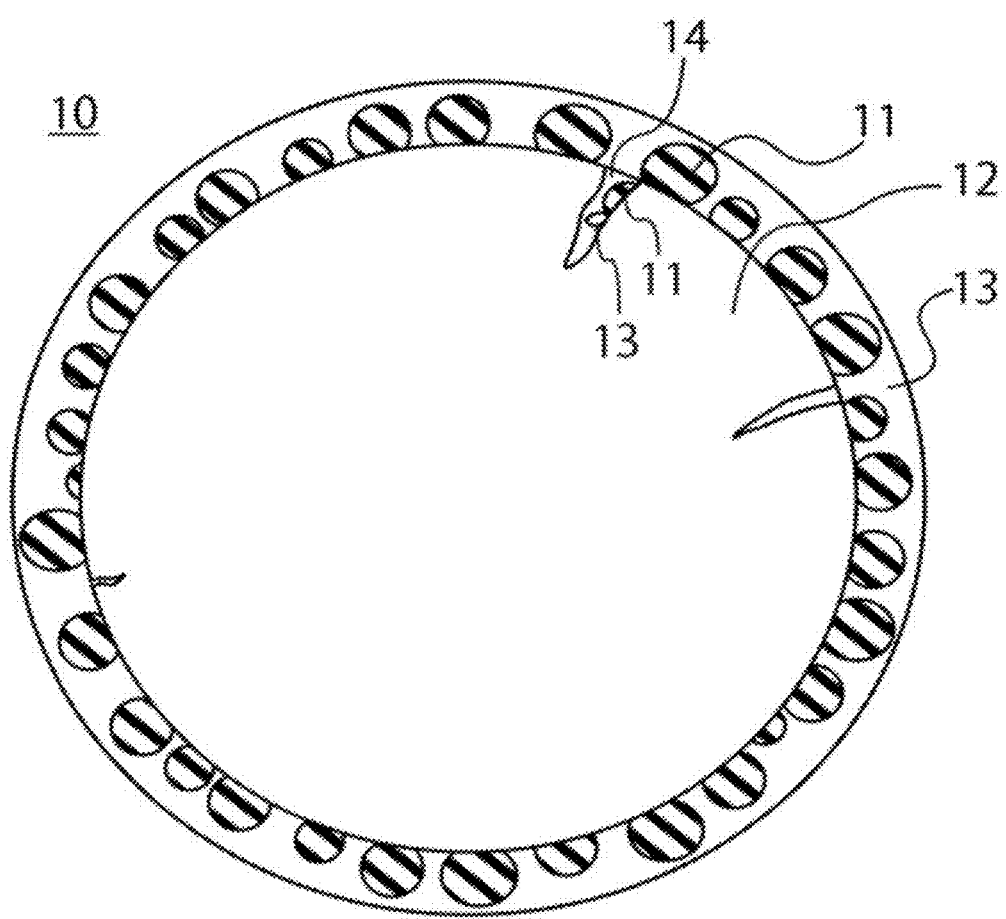
FIG. 1A is a schematic diagram of the cross-sectional structure of a catalyst according to an embodiment.

A fuel synthesis catalyst of an embodiment for hydrogenating a gas includes at least one selected from the group consisting of; carbon dioxide and carbon monoxide, the catalyst comprising, a base material containing at least one oxide selected from the group consisting of; $Al_2O_3$, MgO, $TiO_2$, and $SiO_2$, first metals containing at least one metal selected from the group consisting of; Ni, Co, Fe, and Cu and brought into contact with the base material, and a first oxide containing at least one selected from the group consisting of; $CeO_2$, $ZrO_2$, $TiO_2$, and $SiO_2$ and having an interface with each of the first metals and the base material. The first metals exist on an outer surface of the base material, and on a surface of the base material in fine pores having opening ends on the outer surface of the base material and inside the base material. The first metals and the first oxide exist in the fine pores. The first metals have interfaces with the base material in the fine pores. The first metals exist inside the base material.

Hereinafter, embodiments will be described using methanation reaction of $CO_2$ as an example with reference to drawings.

As a result of intensive studies on a catalyst for synthesizing one or both of hydrocarbon fuel and alcohol fuel at low temperature from CO or $CO_2$ and $H_2$, it was found that when a composite material prepared by precipitating metal particles from the inner portion of ceramic has a structure in which an oxide capable of dissociating CO or $CO_2$ at low temperature is present to have a large contact area, a catalyst having high low-temperature activity and high reliability can be provided. In addition, it was found that when fine particles having at least one selected from the group consisting of; Fe and Co are contained in the oxide, the activity at low temperature can be further increased. Fuel synthesis catalysts of embodiments are catalysts for synthesizing hydrocarbon fuel and alcohol fuel. Therefore, in the embodiments, in terms of the configurations of the catalysts, there is no difference between a hydrocarbon fuel synthesis catalyst and an alcohol fuel synthesis catalyst. A fuel to be generated varies depending on the difference in conditions of reaction using a catalyst, for example, a difference in raw material between carbon monoxide and carbon dioxide. A fuel containing one or both of hydrocarbon fuel and alcohol fuel is synthesized by the catalysts of the embodiments.

First Embodiment

A catalyst according to a first embodiment includes a base material containing at least one selected from the group consisting of; $Al_2O_3$, MgO, $TiO_2$, and $SiO_2$, first metals supported on the base material and containing at least one metal selected from the group consisting of; Ni, Co, Fe, and Cu, and a first oxide brought into contact with each of the first metals and the base material to have interfaces therewith and containing at least one selected from the group consisting of; $CeO_2$, $ZrO_2$, $TiO_2$, and $SiO_2$. Such a catalyst is a fuel synthesis catalyst for hydrogenating a gas containing carbon dioxide and/or carbon monoxide.

Figure 1B:
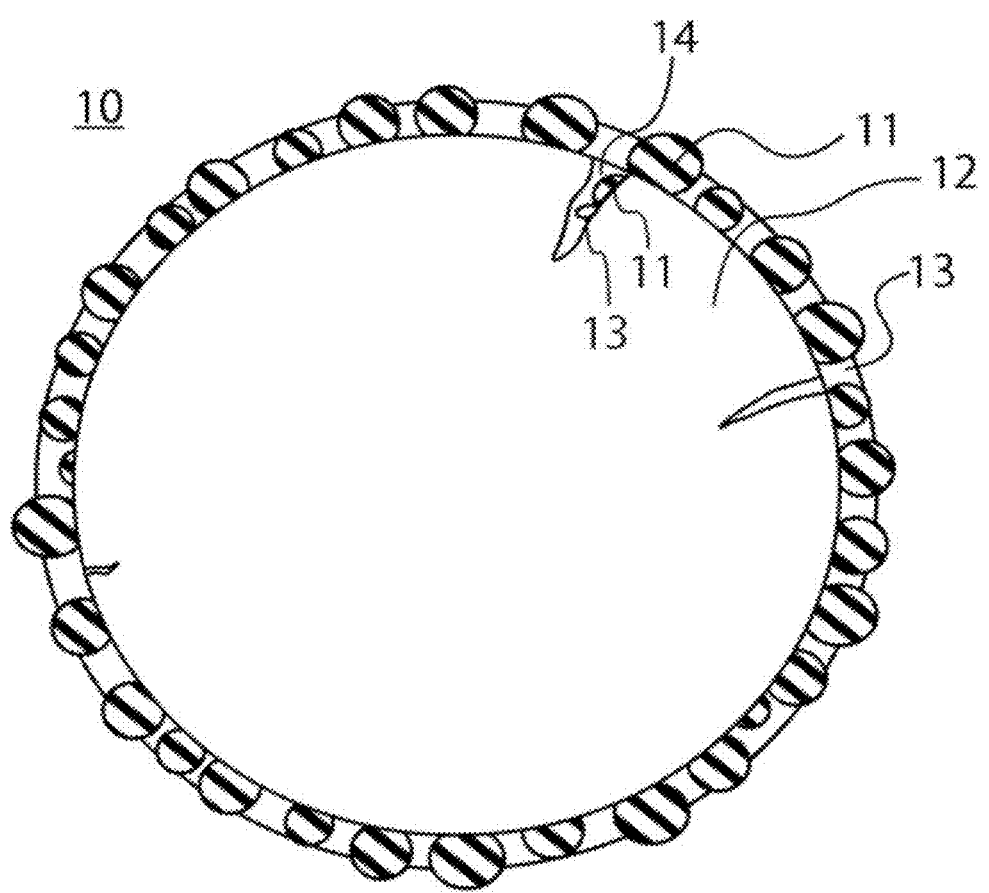
FIG. 1B is a schematic diagram of the cross-sectional structure of the catalyst according to the embodiment.
Figure 1C:
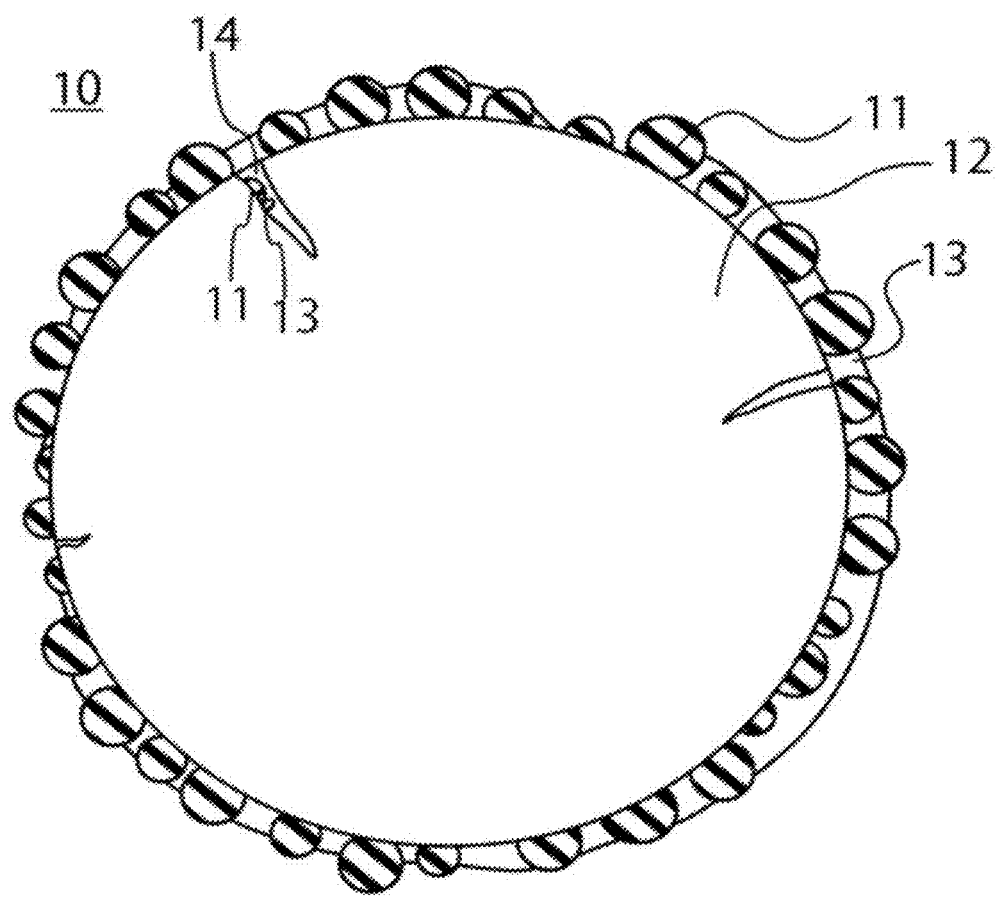
FIG. 1C is a schematic diagram of the cross-sectional structure of the catalyst according to the embodiment.
Figure 2A:
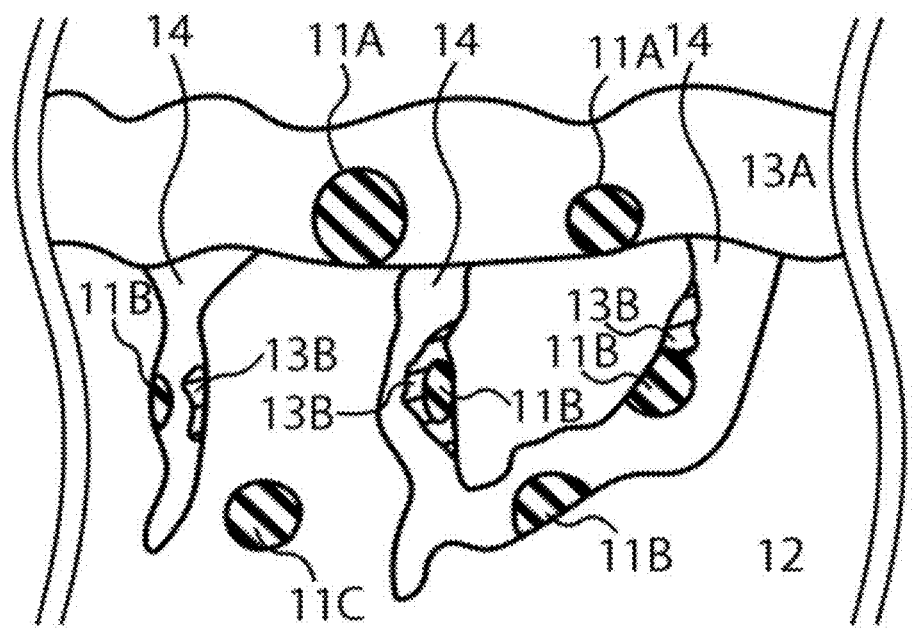
FIG. 2A is an enlarged schematic diagram of the catalyst according to the embodiment.
Figure 2B:
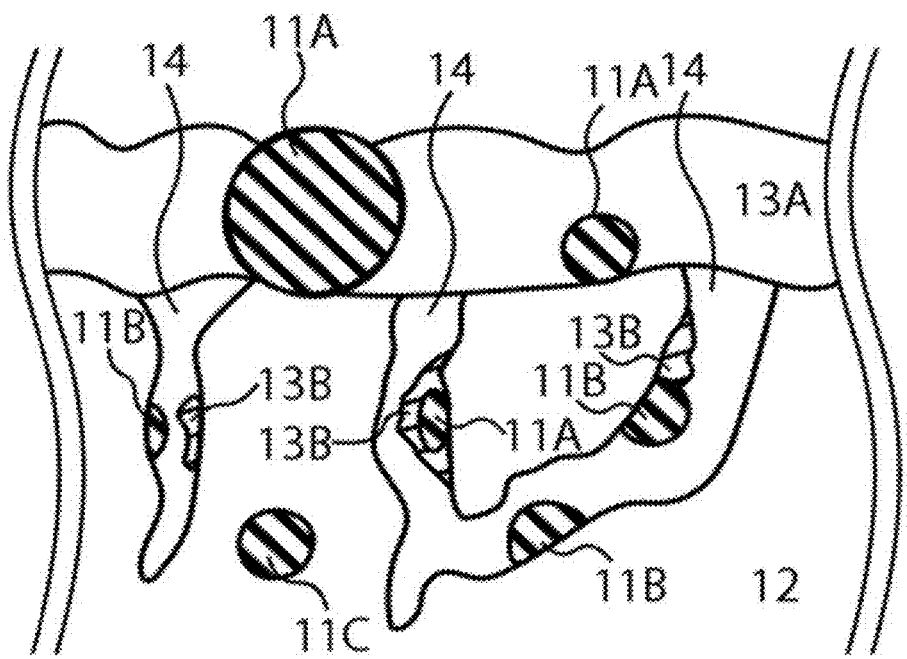
FIG. 2B is an enlarged schematic diagram of the catalyst according to the embodiment.
Figure 2C:
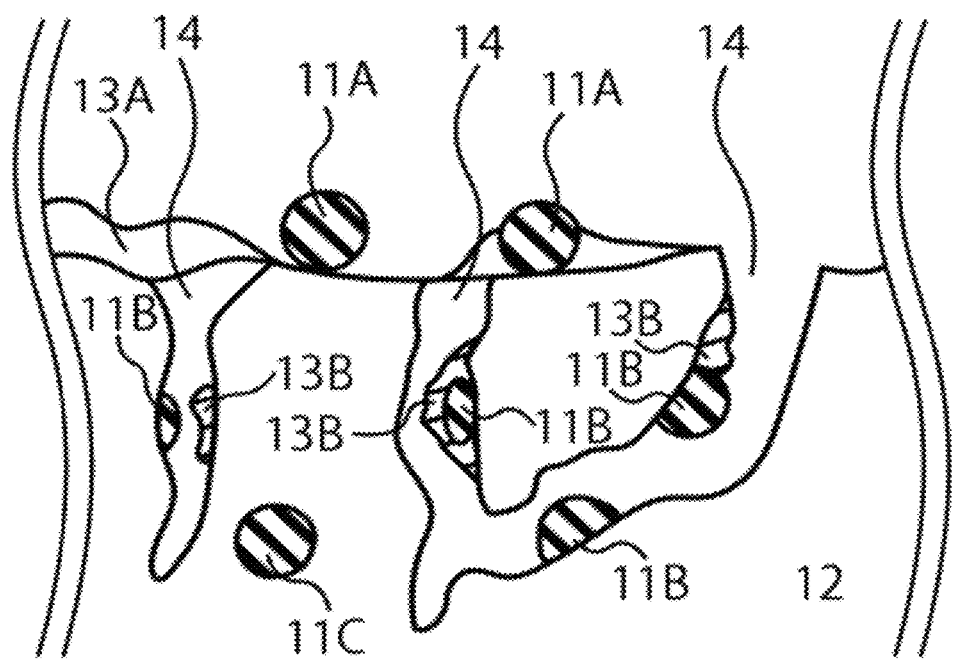
FIG. 2C is an enlarged schematic diagram of the catalyst according to the embodiment.

FIG. 1A, FIG. 1B, and FIG. 1C illustrate schematic diagrams of the cross-sectional structure of a catalyst material according to an embodiment. FIG. 2A, FIG. 2B, and FIG. 2C illustrate enlarged schematic diagrams of parts of FIG. 1A, FIG. 1B, and FIG. 1C.

A catalyst 10 according to the embodiment includes first metals 11, a base material 12, and a first oxide 13. The catalyst 10 according to the embodiment is preferably a catalyst formed by the first metals 11, the base material 12, and the first oxide 13. The first oxide 13 in fine pores 14 of the enlarged diagram is provided with diagonal lines for easy distinction from the other portions. In FIGS. 1A to 1C and FIGS. 2A to 2C, pores other than the fine pores 14 are not illustrated, but a large number of pores are included in the base material 12 and the first oxide 13 since they are porous. In the schematic diagrams of FIGS. 2A, 2B, and 2C, the first metals 11 and the first oxide 13 existing on the outer surface of the base material 12 are referred to as first metals 11A and a first oxide 13A, respectively. The first metals 11 and the first oxide 13 existing in the fine pores 14 are referred to as first metals 11B and a first oxide 13B, respectively. The first metals 11 existing inside the base material 12 are referred to as first metals 11C. Incidentally, existing places of the first metals 11 and the like are distinguished by A, B, and C in the description of FIGS. 2A to 2C. However, in the specification, a case where the description is made without using these alphabets is also included. The outer surface indicates a surface excluding a surface portion in the fine pore among the surfaces.

In the catalyst 10 of the first embodiment, the first metals 11 are brought into contact with the base material 12. The first oxide 13 has an interface with the first metals 11. The first oxide 13 has an interface with the base material 12. The base material 12 includes fine pores 14. Opening ends of the fine pores 14 exist on the outer surface of the base material 12. The first metals 11 and the first oxide 13 exist in the fine pores 14. The first metals 11B and the base material 12 are in direct contact with each other in the fine pores 14, and the first metals 11B have interfaces with the base material 12. Further, it is preferable that the first oxide 13 partially or entirely cover the base material 12 with which the first metals 11 are brought into contact. A configuration in which the first metals 11 are bonded to the base material 12 to be physically brought into surface contact with the base material 12 is preferable.

There are differences between the catalyst 10 of FIG. 1A and the catalyst 10 of FIG. 1B. The first oxide 13 of FIG. 1A covers the first metals 11 and the base material 12; in contrast, the first oxide 13 of FIG. 1B partially covers the first metals 11 and the base material 12 and at least some of the first metals 11 are exposed. In FIG. 1B, the first metals 11 and the base material 12 covered with the first oxide 13 are included. The ratio of coverage and partial coverage with the first oxide 13 can be set to an arbitrary ratio. In the catalyst 10 of FIG. 1C, the first oxide 13 partially covers the base material 12 with which the first metals 11 are brought into contact. The catalyst 10 of FIG. 1C is different from the catalysts 10 of FIG. 1A and FIG. 1B in that some of the first metals 11 are not brought into contact with the first oxide 13 and some of surfaces, which the first metals 11 are not brought into contact with, of the base material 12 are not covered with the first oxide 13. In addition, a combination of cross-sectional forms of FIG. 1A, FIG. 1B, and FIG. 1C may be employed as the catalyst 10 of the embodiment. Incidentally, as a modified example of FIG. 1C, a form in which some of the first metals 11 are not brought into contact with the first oxide 13 but surfaces, which the first metals 11 are not brought contact with, of the base material 12 are covered with the first oxide 13 and a form in which some of surfaces, which the first metals 11 are not brought into contact with, of the base material 12 are not covered with the first oxide 13 but the first metals 11 are brought into contact with the first oxide 13 are mentioned. The first oxide 13 existing on the outer surface of the catalyst 10 is an oxide layer and a covered layer.

As illustrated in FIG. 1A, in the cross-section, in a case where the first oxide 13 entirely covers the base material 12 with which the first metals 11 are brought into contact, the base material 12 is covered with the first metals 11 and the first oxide 13, the first metals 11 have an interface between the first metals 11 and the base material 12 and an interface between the first metals 11 and the first oxide 13, and have no exposed surface.

As illustrated in FIG. 1B, in the cross-section, in a case where the first oxide 13 covers the base material 12 with which the first metals 11 are brought into contact and at least some of the first metals 11 are exposed, the base material 12 is covered with the first metals 11 and the first oxide 13, and the first metals 11 have exposed surfaces, an interface between the first metals 11 and the base material 12, and an interface between the first metals 11 and the first oxide 13. That is, in FIG. 1B, the outer surface of the catalyst 10 does not include the surface of the base material 12 but includes the surfaces of the first metals 11 and the first oxide 13. The first metals 11 and the first oxide 13 exist inside the fine pores 14 having opening ends on the outer surface of the base material 12. As illustrated in FIGS. 1B and 2B, the first metals 11 and the first oxide 13 are in direct contact with the base material 12. More specifically, on the outer surface of the base material 12, the first metals 11A and the first oxide 13A are in direct contact with the base material 12. On the outer surface of the base material 12, the first metals 11A have interfaces with the base material 12. In the fine pores 14 of the base material 12, the first metals 11B and the first oxide 13B are in direct contact with the surfaces of the fine pores 14 of the base material 12. In the fine pores 14, the first metals 11B have interfaces with the base material 12 and the first oxide 13B has an interface with the base material 12. In the fine pores 14, it is preferable that the first metals 11B having interfaces with the base material 12 have interfaces with the first oxide 13B. The first metals 11C are included inside the base material 12. Inside the fine pores 14 of the base material 12, the first metals 11B and the first oxide 13B are in direct contact with each other. A part of the first oxide 13B may cover the first metals 11B in the fine pores 14. Further, as illustrated in FIG. 2B, the fine pores 14 may be connected to each other in the base material 12. In addition, in the fine pores 14, it is preferable that the first metals 11 having interfaces with the base material 12 have interfaces with the first oxide 13.

As illustrated in FIG. 1C, in the cross-section, in a case where the first oxide 13 partially covers the base material 12 with which the first metals 11 are brought into contact, some of the first metals 11 are not brought into contact with the first oxide 13, and some of surfaces, which the first metals 11 are not brought into contact with, of the base material 12 are not covered with the first oxide 13, the base material 12 is partially covered with the first metals 11 and the first oxide 13, and the first metals 11 have exposed surfaces, an interface between the first metals 11 and the base material 12, and an interface between the first metals 11 and the first oxide 13. Some of the first metals 11 have an interface with the base material 12 but do not have an interface with the first oxide 13. That is, in FIG. 1C, the outer surface of the catalyst 10 includes the surfaces of the first metals 11, the surface of the base material 12, and the surface of the first oxide 13. Further, the first metals 11 and the first oxide 13 exist inside the fine pores 14 having opening ends on the outer surface of the base material 12. As illustrated in FIGS. 1C and 2C, the first metals 11 and the first oxide 13 are in direct contact with the base material 12. More specifically, on the outer surface of the base material 12, the first metals 11A and the first oxide 13A are in direct contact with the base material 12. On the outer surface of the base material 12, the first metals 11A have interfaces with the base material 12. In the fine pores 14 of the base material 12, the first metals 11B and the first oxide 13B are in direct contact with the surfaces of the fine pores 14 of the base material 12. In the fine pores 14, the first metals 11B have interfaces with the base material 12 and the first oxide 13B has an interface with the base material 12. In the fine pores 14, it is preferable that the first metals 11B having interfaces with the base material 12 have interfaces with the first oxide 13B. The first metals 11C are included inside the base material 12. Inside the fine pores 14 of the base material 12, the first metals 11B and the first oxide 13B are in direct contact with each other. A part of the first oxide 13B may cover the first metals 11B in the fine pores 14. Further, as illustrated in FIG. 2C, the fine pores 14 may be connected to each other in the base material 12. In addition, in the fine pores 14, it is preferable that the first metals 11 having interfaces with the base material 12 have interfaces with the first oxide 13. Furthermore, the opening ends of the fine pores 14 may exist on the outer surface of the catalyst 10.

The particle diameter of the catalyst 10 is preferably 2 mm or more and 10 mm or less. When the particle diameter of the catalyst 10 is less than 2 mm, in a case where a reaction tube is filled with the catalyst, pressure loss increases, which is not favorable. In addition, when the particle diameter of the catalyst 10 is more than 10 mm, the first metals existing deeply inside the catalyst are not utilized, and thus useless portions increase, which is not favorable. Regarding the particle diameter of the catalyst 10, the catalyst 10 is subjected to slice processing and the processed sample is observed with an optical microscope. 50 particles having the clearest outline of the catalyst in the photographed image are selected, a circumscribed circle diameter $\phi A1$ and an inscribed circle diameter $\phi A2$ of each of 50 particles are obtained, and a value obtained from $(\phi A1+\phi A2)/2$ is designated as the particle diameter of each particle. Then, an average value of particle diameters of 40 particles, excluding five particles having the obtained maximum particle diameter and five particles having the obtained minimum particle diameter, is designated as the average particle diameter of the catalyst 10.

The first metals 11 are particulate metals (metal particles) containing at least one element selected from the group consisting of; Ni, Co, Fe, and Cu. The first metals 11 exist on the outer surface of the base material 12 and on the surface of the base material 12 in the fine pores 14 having opening ends on the outer surface of the base material 12, and the first metals 11 exist inside the base material 12. It is preferable that the first metals 11 exist to be interposed between the base material 12 and the first oxide 13. Some of the first metals 11 may exist inside the base material 12. These first metals are preferably any one of metal particles formed by a single element, metal particles in which a plurality of particles formed by a single element are mixed, alloy particles containing a plurality of elements, and particles in which metal particles and alloy particles are mixed. The first metals 11 are more preferably particles containing at least Ni particles. The first metals 11 are more preferably particles formed by at least one element selected from the group consisting of; Ni, Co, Fe, and Cu, from the viewpoint of obtaining a catalyst which is inexpensive and excellent in low-temperature activity.

The particle diameter of the first metals 11 is preferably in a range of from 2 nm to 200 nm. The reason for this is that particles having a particle diameter of less than 2 nm may less distribute to reaction, and when the particle diameter is more than 200 nm, the specific area of the catalyst may be decreased and adjacent particles are easily aggregated while in use. The range is more preferably 10 nm or more and 150 nm or less in terms of the average particle diameter.

Herein, the particle diameter of the first metals 11 and the average particle diameter thereof will be described. For measurement of the particle diameter of the first metals 11, a surface layer portion of the catalyst 10 that is an area including at least the first metals 11 and includes at least the surface of the base material 12 is observed to obtain the particle diameter. In this case, the catalyst 10 is subjected to slice processing to have a form including the surface layer portion of the catalyst and the vicinity of the surface layer portion is observed by a TEM (Transmission Electron Microscope) with a magnification of 100,000 or more. For the photographing magnification, an appropriate magnification is selected depending on the size of the first metals 11. In a case where the first metals 11 are covered with the first oxide 13 so that the first metals 11 cannot be confirmed, a sample is polished and then a surface in which the first metals 11 can be confirmed may be observed. Then, 50 particles having the clearest outline of the first metals 11 in the photographed image are selected, a circumscribed circle diameter $\phi B1$ and an inscribed circle diameter $\phi B2$ of each of 50 particles are obtained, and a value obtained from $(\phi B1+\phi B2)/2$ is designated as the particle diameter of each particle. As necessary, element specification may be performed by TEM-EDS (Transmission Electron Microscope/Energy dispersive Spectrometry). Then, an average value of particle diameters of 40 particles, excluding five particles having the obtained maximum particle diameter and five particles having the obtained minimum particle diameter, is designated as the average particle diameter of the first metals 11.

The base material 12 is a base material containing at least one metal oxide selected from the group consisting of; $Al_2O_3$, MgO, $TiO_2$, and $SiO_2$. A plurality of these oxides may exist in a mixed state, but the base material 12 is a structural body having a particulate shape with a size suitable for practical use or a honeycomb shape. The first metals 11 and the first oxide 13 exist on the surface of the base material 12, and the first metals 11 and the first oxide 13 are brought into physical contact with the base material 12. It is preferable that the first oxide 13 exist on the surface other than the portion, in which the first metals 11 exist, of the surface of the base material 12, but some of the surfaces of the base material 12 may be exposed surfaces in which neither the first metals 11 nor the first oxide 13 exists.

The base material 12 is formed by a so-called metal/ceramic composite material that is an integral structure with the first metals 11 which are in physical contact with the surface of the base material 12 or the first metals 11 which are in physical contact with the surface of the base material 12 and the first metals 11 which exist inside the base material 12. It is preferable that the first metals 11 be directly bonded to (compounded with) the base material 12 and each particle of the first metals 11 exists on the base material 12 in an independently dispersed manner. It is more preferable that all of the first metals 11 be directly bonded to (compounded with) the base material 12 and each particle of the first metals 11 exists on the base material 12 in an independently dispersed manner. Some of the first metals 11 exist, as illustrated in FIGS. 2A to 2C, in the base material 12 in a precipitated manner. That is, some of the first metals 11 exist on the surface of the base material 12 and some of the first metals 11 exist inside the base material 12. The first metals 11 in the base material 12 are also compounded with the base material 12. Specifically, as illustrated in FIG. 1A and FIG. 1B, at least some of the first metals 11 are buried in the base material 12. Such a structure can be confirmed by observing the cross-sectional portion of the catalyst by a TEM with high magnification. Since the catalyst 10 is obtained by reducing a compound of an easily-reducible oxide and a hardly-reducible oxide, the catalyst 10 has a structure in which the first metals 11 derived from the easily-reducible oxide are precipitated on the surface portion of the base material during reduction. Therefore, it is preferable that the first metals 11, which are in direct contact with the surface of the base material 12, among the first metals 11 have an entirely buried structure (80% or more of the total number of the first metals 11).

Examples of combinations of the first metals 11 and the base material 12 include Ni—$Al_2O_3$, Co—$Al_2O_3$, Fe—$Al_2O_3$, NiCo—$Al_2O_3$, NiFe—$Al_2O_3$, NiCu—$Al_2O_3$, CoFe—$Al_2O_3$, Ni—MgO, Co—MgO, Fe—MgO, NiCo—MgO, NiFe—MgO, NiCu—MgO, CoFe—MgO, Ni—$TiO_2$, Co—$TiO_2$, Fe—$TiO_2$, NiCo—$TiO_2$, NiFe—$TiO_2$, NiCu—$TiO_2$, CoFe—$TiO_2$, Ni—$SiO_2$, Co—$SiO_2$, Fe—$SiO_2$, NiCo—$SiO_2$, NiFe—$SiO_2$, NiCu—$SiO_2$, and CoFe—$SiO_2$. These can be used singly or in combination.

The composite material formed by the first metals 11 and the base material 12 preferably has a porous structure. From the viewpoint of improving the catalyst activity at low temperature, a structure having both of macro pores and micro pores is preferable. Specifically, the composite material preferably has a structure having macro pores, which have a pore diameter of 200 nm or more and 10 μm or less, enabling reaction to act on the catalyst on the deep portion of ceramic and micro pores, which have a pore diameter of 2 nm or more and 30 nm or less, for providing a large reaction area. The fine pores 14 are micro pores having a pore diameter of 2 nm or more and 30 nm or less. The fine pores 14 are not locally but entirely contained in the catalyst 10. It is preferable that the fine pores 14 form a three-dimensional network inside the base material 12. When a lot of the fine pores 14 in which the first metals 11 and the first oxide 13 exist are contained in the catalyst 10, the catalyst performance per volume of the catalyst 10 is improved. Since the fine pores 14 are supply and discharge passages for a reaction raw material and a reaction product, the catalyst 10 of the embodiments is preferable in terms of having excellent catalyst performance on the surface of the catalyst 10 and in the inside thereof (the fine pores 14).

The composition of the oxide contained in the base material 12 is obtained by X-ray diffraction (XRD) measurement.

Further, the porous first oxide 13 containing at least one oxide selected from the group consisting of; $CeO_2$, $ZrO_2$, $TiO_2$, and $SiO_2$ is formed on the outer surface portion of the base material of the metal/composite base material in a state where the first oxide 13 is brought into contact with the first metals 11. These oxides have characteristics of helping CO or $CO_2$, which has been adsorbed once, to be easily dissociated at lower temperature and play an important role of improving the catalyst activity at low temperature. The pore diameter of the first oxide 13 is preferably 2 nm or more and 10 μm or less. In addition, it is preferable that the first oxide 13 also exist in the fine pores 14. It is preferable that the first oxide 13 existing in the fine pores 14 be in direct contact with the first metals 11 and the base material 12 to form an interface.

The first oxide 13 is formed to partially or entirely cover the outer surface of the composite material. The first oxide 13 may be formed to cover the surface portions of the first metals 11 on the outer surface of the catalyst 10 as illustrated in FIG. 1A or may be formed in a state where the first metals 11 on the outer surface of the catalyst 10 are exposed to the surface portion as illustrated in FIG. 1B. As illustrated in FIG. 1C, a part of the base material 12 may have an exposed surface or may include a portion in which some of the first metals 11 are not brought into contact with the base material 12. The first oxide 13 of the outer surface is preferably a porous layer-shaped product having gas diffusivity. The methanation reaction is considered to occur at a so-called three-phase interface in which $CO_2$ (or reduced CO) and hydrogen as reactive species and the first metals 11 as a catalyst are brought into contact with one another. The activity is improved by forming a large number of this three-phase interface. Such a porous structure enables gas to easily come and go and can increase this three-phase interface place. That is, $CO_2$, which has been adsorbed once by the first oxide 13, moved smoothly on the surface of the first metals 11 as a catalyst, and dissociated at low temperature, smoothly reacts with hydrogen on the surface of the first metals 11, or $CO_2$ is easily reduced by oxygen defect, and thus reaction until $CH_4$ is obtained can be performed without remaining CO generated in the course of the reaction. For these reasons, even when the first oxide 13 has the same composition as the base material 12, since the contact area with the first metals 11 is increased as illustrated in FIGS. 1A to 1C, an effect of further activating the reaction at low temperature can be expected.

Since the first oxide 13 is porous, the three-phase interface of the first metals 11 exists even in a case where the first metal 11 has or does not have an exposed surface on the outer surface of the catalyst 10. Instead, since the first oxide 13 forms an interface with the first metals 11, the first oxide 13 supplying CO or $CO_2$ exists in the vicinity of the first metals 11 so that the reaction is promoted. Further, since generated hydrocarbon or alcohol passes through porous pores of the first oxide 13 to be discharged to the outside of the catalyst 10, the first oxide 13 has both functions of supplying a reaction raw material and providing a discharge passage of a product. Moreover, since the first oxide 13 dissociates CO or $CO_2$ at low temperature, low-temperature activity of the catalyst 10 using the first metals 11 is improved by the presence of the first oxide 13.

The thickness of such a first oxide 13 (the thickness of the first oxide 13 existing on the outer surface of the catalyst 10) is preferably at least 10 nm or more in terms of the average value. The reason for this is that with such a thickness of 10 nm or more, the first oxide can be formed to cover some portions of the first metals 11 which are precipitated by reduction. A portion, which is brought into contact with the base material 12, of a general catalyst is almost dot-like; on the other hand, with the above-described configuration, a ridge portion of the first metals 11 can contribute to reaction. The thickness of the first oxide 13 is preferably thicker, but when the thickness is too thick, diffusion of gas is delayed, and thus the thickness is preferably within about 10 μm at most.

Whether the first metals 11 are present in the first oxide 13 can be analyzed by surface observation of the catalyst 10 by a SEM or by observation of the cross-section of the structure by a TEM. For example, the surface portion of the catalyst 10 is observed by a high-resolution SEM. The composition analysis of the surface portion is performed in advance by EDS or the like, a portion where the first oxide 13 such as $CeO_2$ exists is searched, and then the portion is enlarged to at least 10,000 times or more. Then, the acceleration voltage is changed to obtain information in the depth direction and information of the first metals 11, such as Ni, located under the first oxide 13, such as $CeO_2$, can be obtained by performing photographing by a reflected electron image. The pore diameter of the first oxide 13 can be also obtained by the above-described method. Incidentally, also in a case where the base material 12 and the first oxide 13 are formed by the same compound, the cross-section observation described above is performed, and the structure analysis may be performed from the characteristic of the interface where crystallinity (for example grain size) varies.

In addition, the first oxide 13 is more preferably a solid-solubilized product with a second oxide. The second oxide more preferably contains a rare-earth oxide. The rare-earth oxide is an oxide containing at least one element selected from the group consisting of; La, Sm, Gd, and Y. Specific examples of the second oxide include an oxide such as $La_2O_3$, $Sm_2O_3$, $Y_2O_3$, $Sc_2O_3$, $Gd_2O_3$, CaO, or MgO. The reason for this is that when these oxides are solid-solubilized, the crystalline phase of the first oxide 13 is stabilized, oxygen defect is formed, there is a beneficent influence on dissociation behavior of $CO_2$, and the catalyst activity at lower temperature can be improved. It is preferable that these oxides to be solid-solubilized be contained in 10 mol % or more and 60 mol % or less with respect to the number of moles of the first oxide 13.

The content of the first metals 11 in the entire catalyst 10 is preferably 5% by mass or more. When the content is less than 5% by mass, the effect as the catalyst is small. In addition, the content of the first metals 11 is preferably 20% by mass or less. The reason for this is that when the content is more than 20% by mass, a distance between the first metals 11 are decreased, the first metals are easily combined or aggregated while in use (a so-called sintering phenomenon easily occurs), and thus the performance thereof are deteriorated. The content of the first metals 11 in the entire catalyst 10 is more preferably in a range of from 9.4% by mass to 16.2% by mass. The content of the first metals 11 in the entire catalyst 10 is measured by inductively coupled plasma (ICP) analysis.

(Production Method)

Next, the method for producing the catalyst material according to the embodiment will be described.

In the following description, a catalyst having a size of 2 mm or more and 10 mm or less which is suitable for practical use is described as an example, and the embodiment is not limited thereto. For example, a material may be prepared using powder having a large specific area as a base material, and the material may be granulated in a size suitable for practical use by using an inorganic binder or by performing heat treatment.

First, a material that becomes the base material 12 is prepared. The material can be obtained by using powder or granulated powder of $Al_2O_3$, MgO, $TiO_2$, $SiO_2$, or the like and mixed powder thereof, performing molding by adding a binder or the like, and performing heat treatment under the proper conditions. Herein, in the case of using $Al_2O_3$, $Al_2O_3$ of γ phase having a large specific area is preferably used. As the binder, an organic binder, an inorganic binder, or the like is appropriately selected depending on the powder to be used. Regarding molding, extrusion molding, a roll molding method, or the like can be used. The size of a molded body is preferably set to a size suitable for practical use, and is preferably about 2 mm or more and less than 10 mm. There is no particular limitation on the shape of the molded body, and the molded body can be molded or processed in an easily-handled shape such as a spherical shape, a cylindrical shape, a star shape, or a honeycomb shape.

Unless the molded body is molded or processed in a honeycomb shape, in the case of a pellet shape, since the volume of the inner portion, which does almost not contribute to reaction, of the catalyst 10 increases as the particle diameter of the catalyst 10 is larger than necessary, performance of the catalyst per volume is deteriorated. Therefore, the particle diameter of the catalyst 10 is preferably set to a size not exceeding 1 cm.

Next, the surface layer portion is turned into a composite oxide by using the base material 12. A compound containing at least one element selected from the group consisting of; Ni, Co, Fe, and Cu is brought into contact with the porous base material 12 and is subjected to heat reaction, and thus at least the surface layer portion of the base material 12 is turned into a composite oxide. Examples of the compound include nitrate, sulfate, chloride salt, acetate, carbonate, and hydroxide which contain metal elements mentioned in the first metals 11. In order to form a composite oxide up to the inner portion of the base material 12, an impregnation method using a solution technique is preferably used.

For example, a case where spherical particles formed by $\gamma$-$Al_2O_3$ is used as the base material 12 and nickel nitrate hydrate is used as a metal compound will be described as an example. The $\gamma$-$Al_2O_3$ spheres are immersed in an aqueous solution of nickel nitrate, which has been dissolved in a predetermined concentration, subjected to vacuum impregnation, and dried to obtain $\gamma$-$Al_2O_3$ spheres covered with nickel nitrate. The spheres are subjected to heat treatment to thermally decompose nickel nitrate, thereby forming NiO. The method of coating NiO for reacting with $Al_2O_3$ of the base material 12 is not limited thereto. Then, the formed NiO is heated from 1000° C. to 1400° C. so that the base material 12 and NiO generated through thermal decomposition are reacted with each other to thereby obtain a composite base material in which a part of the base material 12 is turned into a $NiAl_2O_4$ composite oxide.

The layer of this composite oxide is formed on the surface portion of the composite base material. The concentration of unreacted $Al_2O_3$ increases toward the inner portion of the base material. Since the original amount of $Al_2O_3$ as the base material 12 is sufficiently large with respect to NiO used in coating, there is no case where NiO remains after heat treatment. The composite oxide layer varies depending on an oxide used in the base material 12, and for example, in the case of the Ni-based catalyst, when the base material to be used is MgO, $Ni_xMg_{1-x}O$ ($0<x<1$) is formed as a main composition, when the base material to be used is $TiO_2$, $NiTiO_3$ is formed as a main composition, and when the base material to be used is $SiO_2$, $Ni_2SiO_4$ is formed as a main composition. Similarly, the same applies to other metal species, Co, Fe, and Cu.

Next, the first oxide 13 is formed on the composite base material having the composite oxide layer prepared as described above. Examples of the forming method include a method in which the first metals 11 are precipitated by reduction treatment and then are covered with the first oxide 13 and a method in which the first oxide 13 is covered on the composite oxide layer and then the first metals 11 are precipitated by reduction treatment. In both methods, the first metals 11 are precipitated by reductive precipitation.

The former performs composite oxide reduction treatment before forming the first oxide 13. The latter performs composite oxide reduction treatment after forming the first oxide 13. The reduction treatment is performed at a temperature range of 600 to 1100° C. in a reducing atmosphere such as hydrogen. The reducing atmosphere is not limited thereto, and heat treatment may be performed in the presence of a carbon material and in an inert atmosphere such as Ar. In a case where the reduction temperature is lower than 600° C., precipitation of the first metals 11 by reduction is not sufficiently performed, and in a case where the reduction temperature is higher than 1100° C., the precipitated particles are aggregated or coarsened, which is not favorable. The proper reduction temperature varies depending on a composite oxide, and for example, in the case of $Co_2TiO_4$ or the like, the reduction temperature is preferably about 700° C. The proper temperature can be determined by performing thermogravimetric analysis on the composite oxide in a reducing atmosphere. The reduction time is properly about 1 minute to 1 hour. Through the above-described treatments, the composite oxide is reduced, the incorporated metal component becomes fine particles, the fine particles are precipitated to mostly the surface of the base material 12 and partly the inner portion of the base material 12, and thus the metal-ceramic composite material is obtained. At this time, the first metals 11 are formed on the base material 12 in a state where the first metals 11 independently are highly dispersed.

Next, the first oxide 13 of at least one selected from the group consisting of; $CeO_2$, $ZrO_2$, $TiO_2$, and $SiO_2$ is formed on the ceramic to which the first metals 11 are precipitated. This first oxide 13 may be a single oxide or a mixture of a plurality of oxides. In addition, since $CeO_2$, $ZrO_1$, or the like stabilizes the structure as the phase and forms oxygen defect, the second oxide may be solid solution in the first oxide 13. At this time, the solid-solubilized product is contained in at least a part of the first oxide 13 or the entire of the first oxide 13 may be a solid-solubilized product. Such a solid-solubilized product can be produced by, for example, performing impregnation, coating, and heat calcination on an aqueous solution prepared by mixing a plurality of metal salts. It should be noted that in some aqueous solutions, a metal component such as Ni may be easily eluted. In this case, the precipitated first metals 11 are treated to be turned into an oxide by performing heat treatment in air, and then impregnated and covered so that a solid-solubilized product can be formed. The latter producing method is different from the former producing method only in order of treatments, and has the same treatment method as in the former producing method. Therefore, the description of the latter producing method is not provided.

Some of the first oxide 13 and the base material 12 may be reacted with each other during heat treatment. For example, $CeO_2$ as the first oxide 13 and $Al_2O_3$ of the base material 12 may be reacted with each other to form $CeAl_2O_3$, but this phase itself also contributes to improvement in catalyst activity.

Second Embodiment

A catalyst according to a second embodiment includes a base material containing at least one oxide selected from the group consisting of; $Al_2O_3$, MgO, $TiO_2$, and $SiO_2$, first metals brought into contact with the base material and containing at least one metal selected from the group consisting of; Ni, Co, Fe, and Cu, a porous first oxide brought into contact with the first metals and the base material and containing at least one selected from the group consisting of; $CeO_2$, $ZrO_2$, $TiO_2$, and $SiO_2$, and second metals. Herein, a main component of the second metals preferably contains a metal different from a metal included in the first metals among at least one metal selected from the group consisting of; Ni, Co, Fe, and Cu.

Figure 3A:
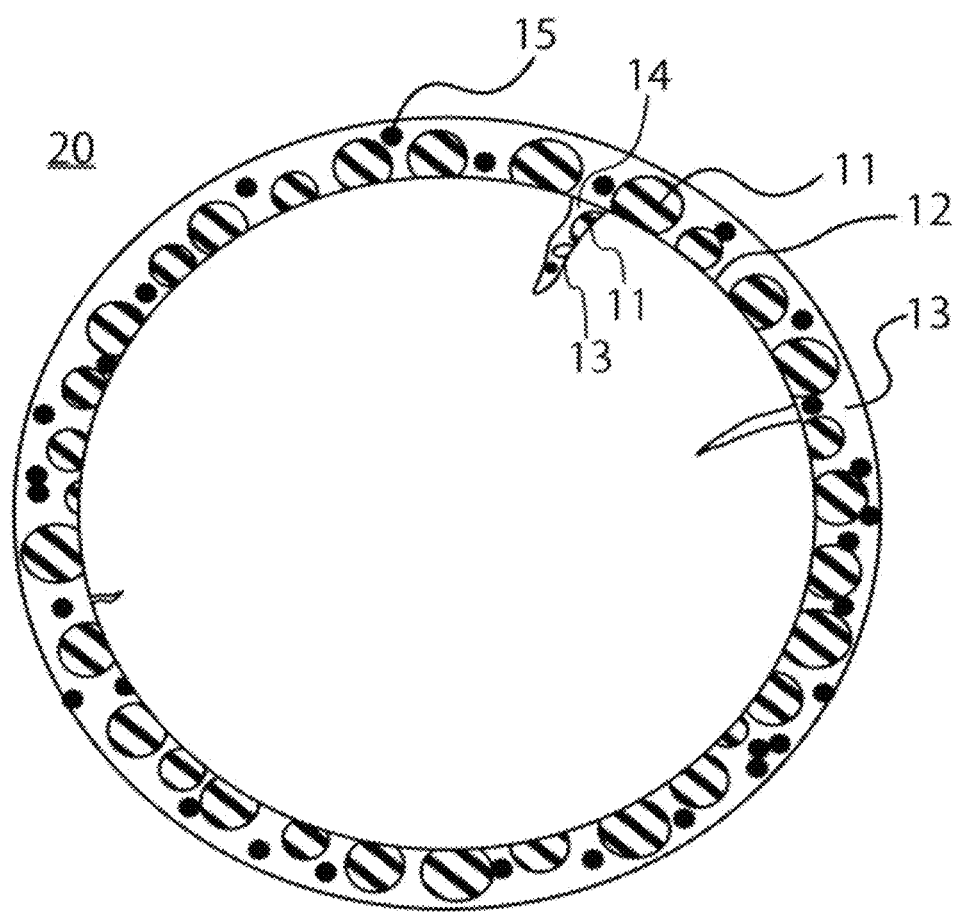
FIG. 3A is a schematic diagram of the cross-sectional structure of a catalyst according to an embodiment.
Figure 3B:
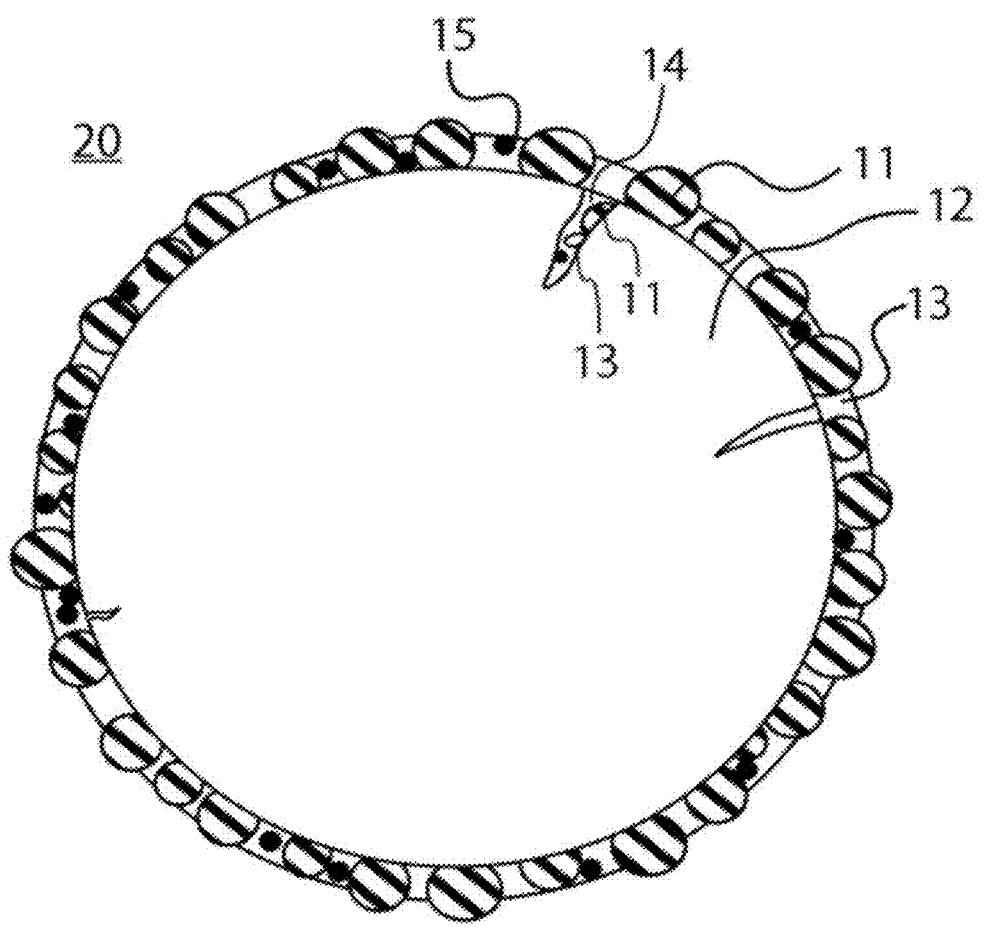
FIG. 3B is a schematic diagram of the cross-sectional structure of the catalyst according to the embodiment.
Figure 3C:
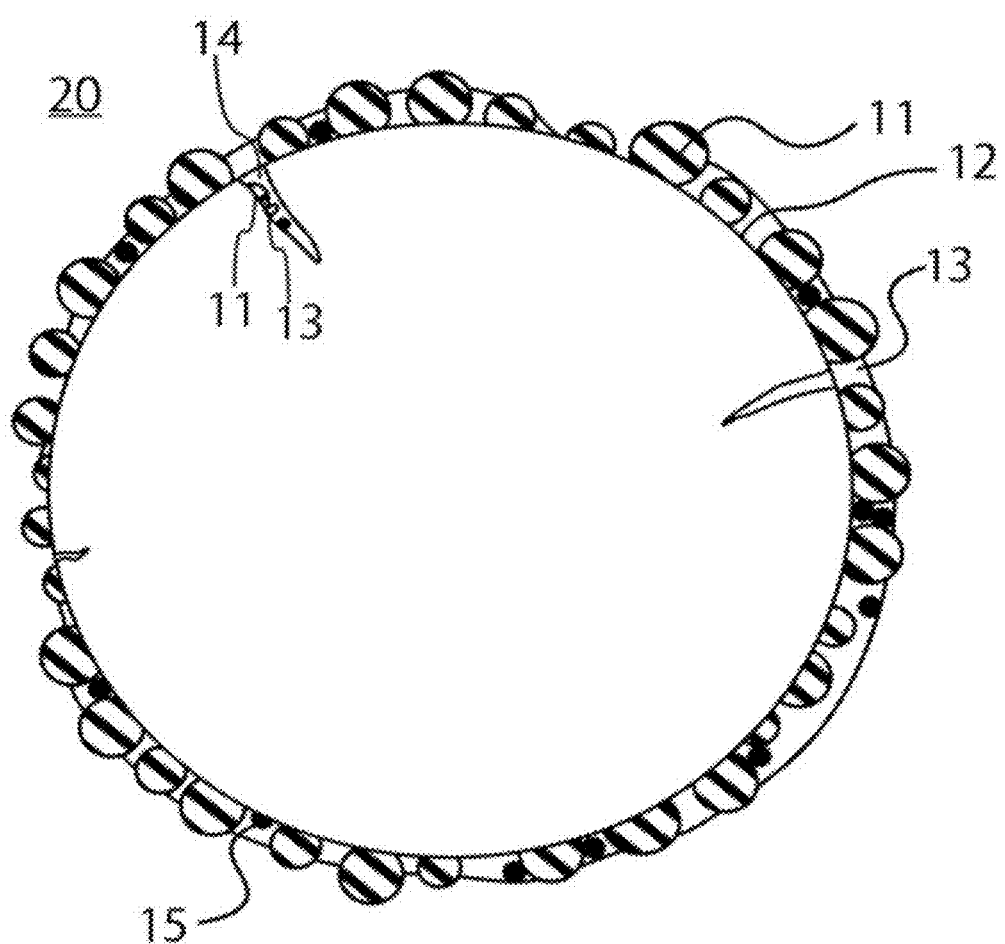
FIG. 3C is a schematic diagram of the cross-sectional structure of the catalyst according to the embodiment.
Figure 4A:
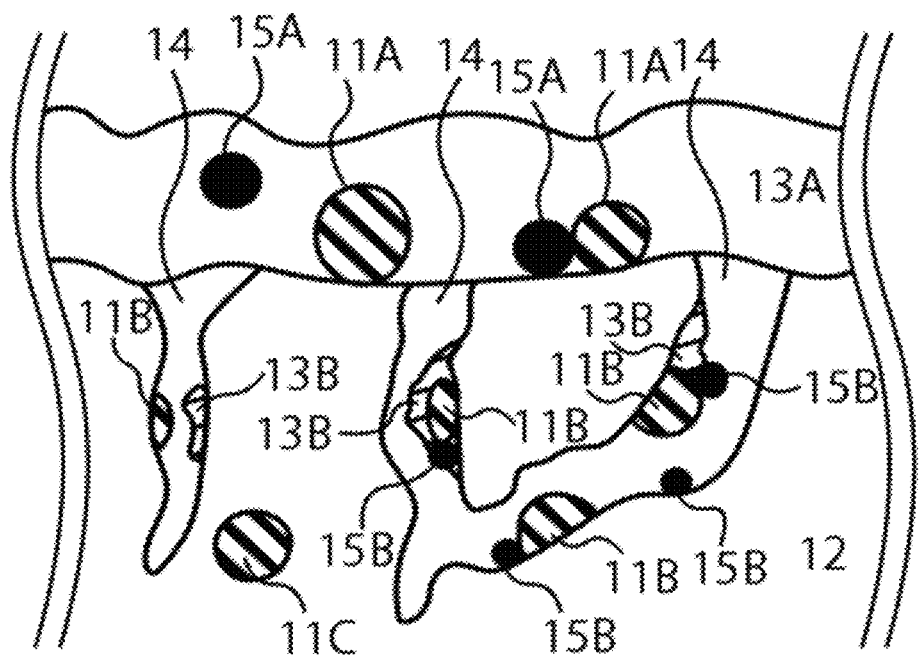
FIG. 4A is an enlarged schematic diagram of the catalyst according to the embodiment.
Figure 4B:
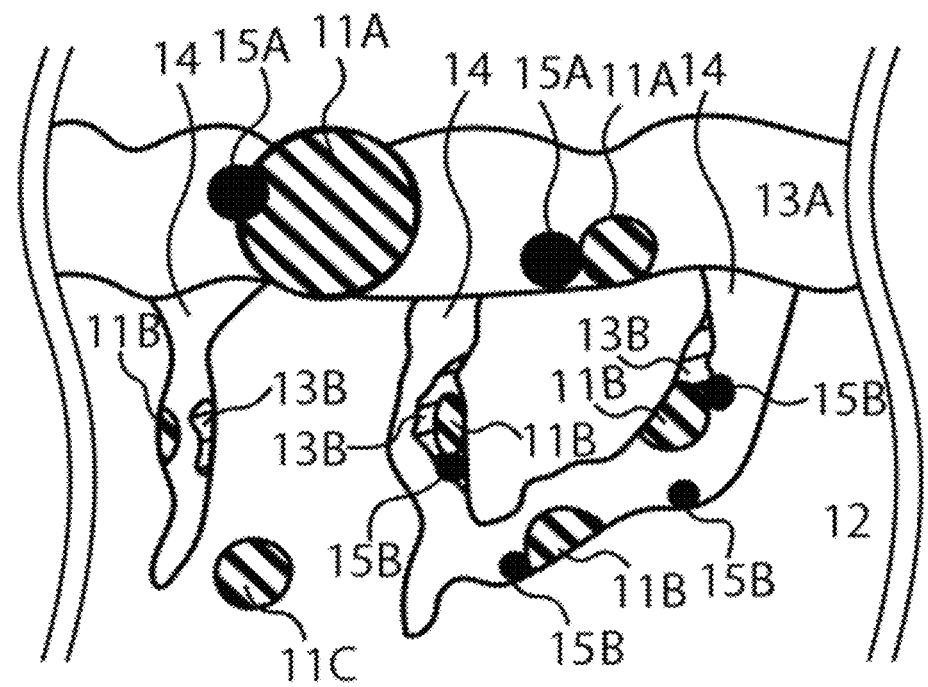
FIG. 4B is an enlarged schematic diagram of the catalyst according to the embodiment.
Figure 4C:
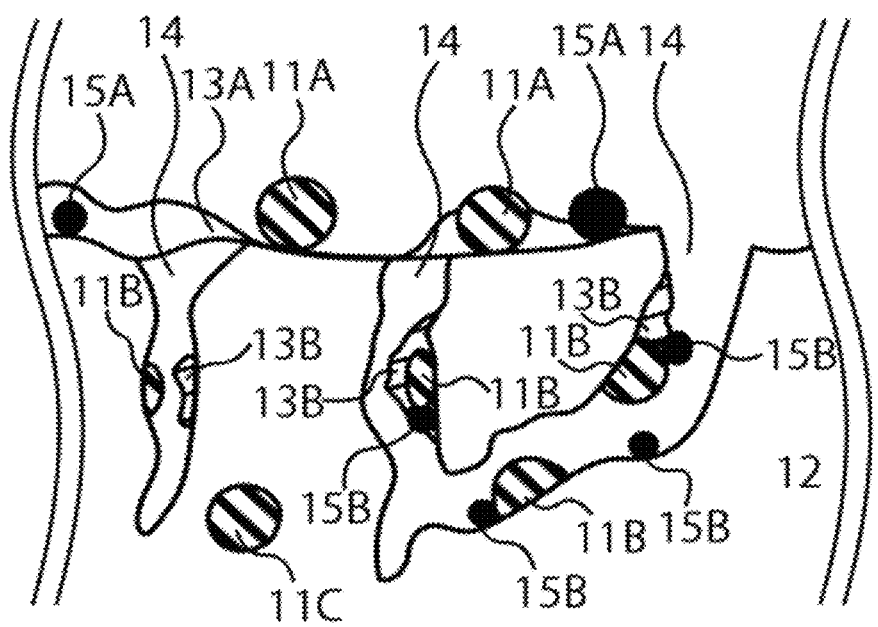
FIG. 4C is an enlarged schematic diagram of the catalyst according to the embodiment.

FIGS. 3A to 3C illustrate schematic diagrams of the cross-section of a catalyst 20 according to the second embodiment (FIGS. 3A to 3C illustrating two structures similarly to the first embodiment). The basic configurations of materials other than second metals 15 are the same as those in the first embodiment, and thus the details thereof are not provided. FIG. 3A, FIG. 3B, and FIG. 3C are different from the cross-sectional views of FIG. 1A, FIG. 1B, and FIG. 1C in that the second metals 15 represented as black dots are included. The characteristic of the catalyst 20 in the second embodiment is that the first oxide 13 has the second metals 15 different from the first metals 11 which are formed by reductive precipitation. In FIGS. 3A to 3C, the primary particle diameter of the second metals 15 is smaller than the primary particle diameter of the first metals 11, but the magnitude relation between the particle diameters is not limited thereto. Incidentally, FIGS. 4A, 4B, and 4C illustrate enlarged schematic diagrams of parts of FIGS. 3A, 3B, and 3C. The enlarged schematic diagrams of FIGS. 4A, 4B, and 4C are also similar to the enlarged schematic diagrams of FIGS. 2A to 2C, except that the second metals 15 exist in the first oxide 13 and the fine pores 14. In FIGS. 4A to 4C, similarly to FIGS. 2A to 2C, the second metals 15 existing in the first oxide 13A on the outer surface of the catalyst 10 are referred to as second metals 15A, and the second metals 15 existing in the fine pores 14 are referred to as second metals 15B.

In FIGS. 4A to 4C, the second metals 15 are contained in the catalyst 10. In all of FIGS. 4A to 4C, the second metals 15A exist in the first oxide 13A. The second metals 15A may have interfaces with the first metals 11A. Further, the second metals 15B exist in the fine pores 14. The second metals 15B existing in the fine pores 14 have interfaces with the first oxide 13B. It is preferable that the second metals 15B existing in the fine pores 14 have interfaces with the first metals 11B. The second metals 15B existing in the fine pores 14 may also have interfaces with the base material 12 and it is preferable that the second metals 15B be in direct contact with the base material 12.

The second metals 15 described herein are particulate metals (particles) including a metal different from a metal included in the first metals among at least one metal selected from the group consisting of; Ni, Co, Fe, and Cu. The size of the second metals 15 is preferably 1 nm or more and 100 nm or less in terms of the primary particle diameter. The particle diameter of the second metals 15 is obtained in the same method as in the first metals 11. Several particles may be aggregated to form secondary particles. The second metals 15 exist in the first oxide 13, or in the first oxide 13 and in the fine pores 14. The second metals 15 may exist in the first oxide 13 while being brought into contact with the base material 12 and the first metals 11 or may exist in the first oxide 13 while being separated therefrom. In addition, the second metals 15 may exist on the surface portion while being brought into contact with the first oxide 13. However, it is more preferable that the second metals 15 exist in the vicinity of the first metals 11 since the second metals 15 act as a cocatalyst of the first metals 11. It is more preferable that the second metals 15 have interfaces with the first metals 11. When the second metals 15 exist in the first oxide 13, an effect is also achieved in which the second metals 15 are immobilized and the aggregation of particles caused by sintering is suppressed so that durability is improved. It is more preferable that the second metals 15 exist also in the fine pores 14. It is preferable that the second metals 15 have interfaces with the first metals 11 and the base material 12 since the second metals act as a cocatalyst. The second metals 15 have interfaces with the first metals 11 in the fine pores 14. However, it is more preferable that the second metals 15 have interfaces with the first metals 11 and the base material 12. Further, it is more preferable that the second metals 15 also have interfaces with the first oxide 13.

The second metals 15 exhibit higher catalyst activity particularly in a case where the second metals 15 are combined with Ni as the first metals 11. In addition, the proportion of the first metals 11 and the second metals 15 in the entire catalyst 20 is preferably 5% by mass or more and 20% by mass or less. The reason for this is as follows. When the proportion is less than 5% by mass, the effect as the catalyst 20 is small. When the proportion is more than 20% by mass, although there is no serious problem in the catalyst activity, the aggregation of metal particles occurs by sintering or the like in the case of long-term use, and thus the performance is deteriorated. From the viewpoint of efficiently utilizing the catalyst 20 without waste, the proportion is more preferably in a range of from 5% by mass to 15% by mass.

A particle diameter of the first metals 11 in which a cumulative volume curve in particle size distribution is 16% is preferably larger than a particle diameter of the second metals 15 in which a cumulative volume curve in particle size distribution is 84%. That is, the size of the first metals 11 is larger than the size of the second metals 15 such that the particle size distribution of the first metals 11 and the particle size distribution of the second metals 15 do almost not overlap. When such a relation is satisfied, it is not easily inhibited that the second metals 15 are contained in the catalyst 20, and this contributes to improvement in catalyst activity. It is considered that the first metals 11 act as a cocatalyst when the second metals 15 smaller than the first metals 11 in size exist in the vicinity of the first metals 11. For example, when Ni with high hydrogenation activity is used as the first metals 11 and Fe with hydrogenation activity lower than that of Ni is used as the second metals 15, catalyst activity is further improved, which is preferable. When the size of the second metals 15 is adjusted to be finer than the size of the first metals 11 such that the above particle size distribution is satisfied, the effect of improving catalyst activity with respect to the amount of the second metals 15 added becomes more significant, which is preferable.

As the method for producing the catalyst 20 containing the second metals 15, for example, a method is mentioned in which a mixed oxide layer is formed on a composite oxide such that the oxide of the second metals 15 that is an easily-reducible oxide is contained in the first oxide 13 and then reduction treatment is performed.

(Fuel Synthesis Apparatus (System))

Figure 5:
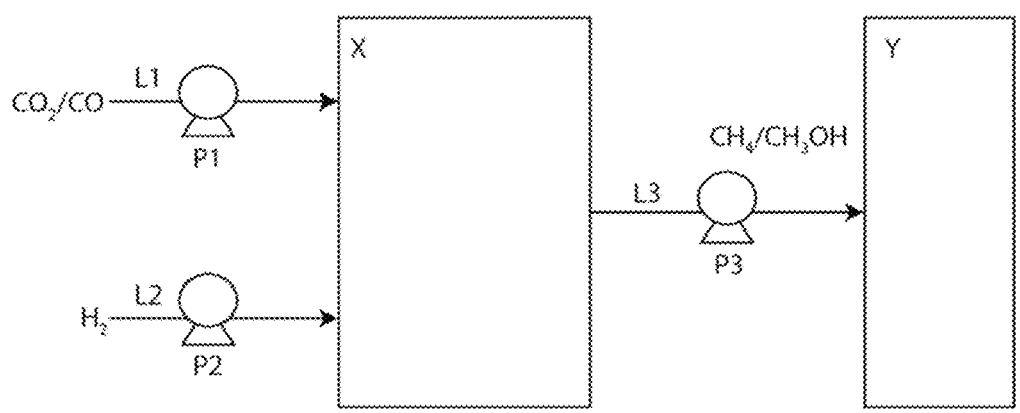
FIG. 5 is a schematic diagram of a fuel synthesis system according to an embodiment.

Next, with reference to the schematic diagram of FIG. 5, a fuel synthesis apparatus (system) using the catalyst of the embodiment will be described. The fuel synthesis apparatus includes a reaction column X provided with the fuel synthesis catalyst, a first raw material supply line L1 configured to supply one or both of carbon dioxide and carbon monoxide to the reaction column, a second raw material supply line L2 configured to supply hydrogen to the reaction column X, and a recovery unit Y configured to recovery a fuel generated by reacting one or both of the carbon dioxide and the carbon monoxide with the hydrogen using the catalyst in the reaction column X.

The reaction column X and the recovery unit Y are connected via a product supply line L3, and the fuel generated in the reaction column X moves from the reaction column X to the recovery unit Y through the product supply line L3. It is preferable that impurities in the product be removed in the recovery unit Y. The fuel generated in reaction column contains one or both of hydrocarbon fuel and alcohol fuel. In addition, although not illustrated in the drawing, the fuel synthesis apparatus is preferably configured such that unreacted carbon dioxide or carbon monoxide and hydrogen are separated from each other in the recovery unit Y and the separated components are sent to the reaction column X to be used for reaction. In addition, the recovery unit Y may further include a unit configured to consume fuel, for example, generate power using the fuel.

The temperature of reaction of the carbon dioxide or carbon monoxide with the hydrogen using the catalyst is preferably 250° C. or higher but 400° C. or lower. When the temperature is too low, the catalyst activity is lowered, which is not favorable. In addition, when the temperature is too high, deterioration of the catalyst is accelerated and energy necessary for reaction is required much more, which is not favorable. From these points of view, the temperature of reaction of the carbon dioxide or carbon monoxide with the hydrogen using the catalyst is more preferably 300° C. or higher but 350° C. or lower. At such a low temperature, a catalyst of the related art has low catalyst activity and thus is not suitable for practical use; on the other hand, the catalyst of the embodiment has excellent low-temperature activity and thus is suitable for practical use even at low-temperature conditions.

Figure 6:
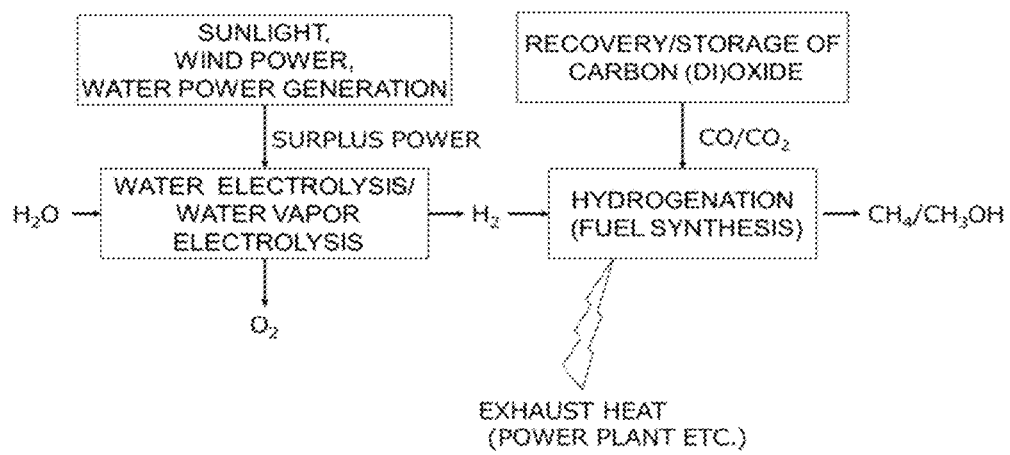
FIG. 6 is a schematic diagram of power generation and the fuel synthesis system according to the embodiment.

In addition, as illustrated in the schematic diagram of FIG. 6, the power generation and the fuel synthesis apparatus (system) may be combined. Hydrogen generated by performing water electrolysis using electric power (surplus power) generated by sunlight or wind power can be used as hydrogen used in the fuel synthesis. In addition, when carbon dioxide generated by thermal power generation or the like is used as carbon dioxide used in fuel synthesis, fuel synthesis that is carbon-neutral and uses renewable energy can be performed.

EXAMPLES

Hereinafter, specific examples will be mentioned and the effect thereof will be described. However, embodiments are not limited to these examples.

Example 1

A catalyst material was prepared under the conditions as described below.

γ-$Al_2O_3$ spherical particles having a particle diameter of 2 to 4 mm were immersed in an aqueous solution of nickel nitrate ($Ni(NO_3)_2 \cdot 6H_2O$) and subjected to impregnation treatment for 2 hours under reduced pressure in a vacuum desiccator. A sample was taken out and subjected to dry treatment, and then heat treatment was performed at 500° C. for 1 hour in air with an electrical furnace so that nickel nitrate was thermally decomposed to obtain NiO. Further, the NiO was reacted with $Al_2O_3$ of the base material by increasing the temperature to 1200° C. and performing calcination treatment for 2 hours so that some of $Al_2O_3$ of the base material became $NiAl_2O_4$ that is the composite oxide. Next, this calcined sample was subjected to reduction treatment at 1000° C. for 10 minutes in hydrogen so that first metals of Ni were precipitated from $NiAl_2O_4$ portion. Further, the sample subjected to reduction was immersed in an aqueous solution of cerium nitrate ($Ce(NO_3)_3 \cdot 6H_2O$) and after the resultant solution was dried, heat treatment was performed at 500° C. for 1 hour so that a $CeO_2$ layer was formed as the first oxide on the catalyst surface. The catalyst performance evaluation test was carried out using this sample. As a result of evaluation of the composition of this sample by ICP emission spectrometry, the content of Ni was 9.4% by mass.

(Catalyst Performance Evaluation Test)

For the test, a fixed-bed flow type reaction apparatus was used. A reaction tube having an inner diameter of 42.8 mm was charged with the catalyst mixed with $Al_2O_3$ spheres (average size of 3 mm) unrelated to the reaction, hydrogen reduction was performed at 400° C. for 1 hour, and then a gas prepared by mixing $CO_2$ and $H_2$ at a flow ratio of 1:4 was supplied at a space velocity of 6000/h. The $CO_2$ conversion and methane yield at from 250° C. to 400° C. were obtained by analyzing the outlet gas after the reaction by micro gas chromatograph. The methane yield was calculated by the following equation.

$$\text{Methane yield} = CO_2 \text{ conversion} \times \text{methane selectivity} \qquad (2)$$

Further, for some samples, identification of the constituent phase by XRD and measurement of micro pore distribution by a nitrogen adsorption method and a mercury intrusion method were carried out. In addition, the microstructure of the sample was observed by a SEM.

Comparative Example 1

In Example 1, a sample not subjected to coating treatment using cerium was prepared, and the catalyst performance evaluation test was performed.

Example 2

In Example 1, the reduction treatment of the composite oxide and the formation of the $CeO_2$ layer were performed in the reverse order, that is, impregnation and coating treatment with cerium nitrate was performed before the reduction treatment at 1000° C., the resultant product was subjected to heat treatment at 500° C., and then reduction treatment was performed at 1000° C. for 10 minutes. The catalyst performance evaluation test using the obtained sample was performed. In the case of preparation in this order, the covered $CeO_2$ layer was reacted with $Al_2O_3$ as the base material at the time of reduction to form $CeAlO_3$.

Example 3

A sample was prepared in the same manner as Example 1, except that γ-$Al_2O_3$ spherical particles in which micro pores having a size of several nm were increased in amount and relatively large pores having a size of about 1 μm were also contained were used as the base material, and the catalyst performance evaluation test was performed. As a result of evaluation of the composition of this sample by ICP emission spectrometry, the content of Ni was 16.2% by mass.

Example 4

A sample was prepared in the same procedures as in Example 1, except that a mixed aqueous solution of cerium nitrate and samarium nitrate ($Sm(NO_3)_3 \cdot 6H_2O$) at a molar ratio of 1:0.2 was used in the formation treatment of the $CeO_2$ layer, and the catalyst performance evaluation test was performed.

Example 5

A sample was prepared in the same procedures as in Example 1, except that a mixed aqueous solution of cerium nitrate and yttrium nitrate ($Y(NO_3)_3 \cdot 6H_2O$) at a molar ratio of 1:0.2 was used in the formation treatment of the $CeO_2$ layer, and the catalyst performance evaluation test was performed.

Example 6

A sample was prepared in the same procedures as in Example 1, except that a mixed aqueous solution of cerium nitrate and gadolinium nitrate ($Gd(NO_3)_3 \cdot 6H_2O$) at a molar ratio of 1:0.2 was used in the formation treatment of the $CeO_2$ layer, and the catalyst performance evaluation test was performed.

Example 7

A sample was prepared in the same procedures as in Example 1, except that a mixed aqueous solution of cerium nitrate and lanthanum nitrate ($La(NO_3)_3 \cdot 6H_2O$) at a molar ratio of 1:0.2 was used in the formation treatment of the $CeO_2$ layer, and the catalyst performance evaluation test was performed.

Example 8

A sample was prepared in the same procedures as in Example 1, except that a mixed aqueous solution of cerium nitrate and lanthanum nitrate ($La(NO_3)_3 \cdot 6H_2O$) at a molar ratio of 1:0.4 was used in the formation treatment of the $CeO_2$ layer, and the catalyst performance evaluation test was performed.

Example 9

A sample was prepared in the same procedures as in Example 1, except that the concentration of cerium nitrate was changed to twice that of cerium nitrate in the formation treatment of the $CeO_2$ layer, and the catalyst performance evaluation test was performed.

Example 10

An aqueous solution of zirconium oxynitrate ($ZrO(NO_3)_2 \cdot 2H_2O$) was used for forming the $ZrO_2$ layer instead of the formation of the $CeO_2$ layer, instead of cerium nitrate. Since a phenomenon that Ni of metal was eluted in the aqueous solution of zirconium oxynitrate was observed, Ni precipitated by reduction was subjected to oxidation treatment in advance to form NiO, and then impregnation and coating treatment was performed. A sample was prepared in the same procedures as in Example 1 except the above-described procedures, and the catalyst performance evaluation test was performed.

Example 11

A sample was prepared in the same procedures as in Example 5, except that a mixed aqueous solution of zirconium oxynitrate and samarium nitrate at a molar ratio of 1:0.2 was used for forming the $ZrO_2$ layer instead of the $CeO_2$ layer, and the catalyst performance evaluation test was performed.

Example 12

A sample was prepared in the same procedures as in Example 10, except that a mixed aqueous solution of zirconium oxynitrate and yttrium nitrate at a molar ratio of 1:0.2 was used for forming the $ZrO_2$ layer, and the catalyst performance evaluation test was performed.

Example 13

A sample was prepared in the same procedures as in Example 10, except that a mixed aqueous solution of zirconium oxynitrate and gadolinium nitrate at a molar ratio of 1:0.2 was used for forming the $ZrO_2$ layer, and the catalyst performance evaluation test was performed.

Example 14

A sample was prepared in the same procedures as in Example 10, except that a mixed aqueous solution of zirconium oxynitrate and lanthanum nitrate at a molar ratio of 1:0.2 was used for forming the $ZrO_2$ layer, and the catalyst performance evaluation test was performed.

Example 15

A sample was prepared by changing the order of the reduction treatment and the oxide layer formation treatment in Example 10, and the catalyst performance evaluation test was performed.

Example 16

A sample was prepared in the same procedures as in Example 5, except that a mixed aqueous solution of zirconium oxynitrate and cerium nitrate at a molar ratio of 1:1 was used for forming the $ZrO_2$ layer, and the catalyst performance evaluation test was performed.

Example 17

A sample was prepared in the same procedures as in Example 1, except that hydrolysis of tetraethyl orthosilicate (TEOS) and condensation reaction were used for forming the $SiO_2$ layer instead of the $CeO_2$ layer, and the catalyst performance evaluation test was performed.

Example 18

A sample was prepared in the same procedures as in Example 1, except that titanium tetraethoxide ($Ti(OCH_2H_5)_4$) was used and hydrolysis and heat treatment were performed for forming the $TiO_2$ layer instead of the $CeO_2$ layer, and the catalyst performance evaluation test was performed.

Comparative Example 2

An aqueous solution of nickel nitrate was subjected to vacuum impregnation by using a cylindrically-formed MgO porous body as the base material. After drying, the MgO surface layer portion and the Ni component were reacted with each other by heat treatment at 1200° C. for 2 hours to form a solid-solubilized product of MgO and NiO ($Ni_xMg_{1-x}O$, $0<x<1$). The solid-solubilized product was subjected to reduction treatment at 1000° C. for 10 minutes in a hydrogen atmosphere to obtain a catalyst material having Ni particles on the surface layer portion. The catalyst performance evaluation test on this material was performed.

Example 19

A catalyst material having Ni particles on the surface layer portion of Comparative Example 2 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

Example 20

A sample was prepared in the same procedures as in Example 10, except that zirconium oxynitrate was used in a $ZrO_2$ layer and a $ZrO_2$ layer was formed, and the catalyst performance evaluation test was performed.

Comparative Example 3

An aqueous solution of nickel nitrate was subjected to vacuum impregnation by using a spherically-formed $TiO_2$ porous body having a particle diameter of 2 to 4 mm as the base material. After drying, the $TiO_2$ surface layer portion and Ni component were reacted with each other by heat treatment at 1300° C. for 2 hours to form a $NiTiO_3$ layer. The $NiTiO_3$ layer was subjected to reduction treatment at 800° C. for 10 minutes in a hydrogen atmosphere to obtain a catalyst material having Ni particles on the surface layer portion. The catalyst performance evaluation test on this material was performed.

Example 21

A catalyst material having Ni particles on the surface layer portion of Comparative Example 3 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

Comparative Example 4

An aqueous solution of nickel nitrate was subjected to vacuum impregnation by using a spherically-formed $SiO_2$ porous body having a particle diameter of 2 to 4 mm as the base material. After drying, the $TiO_2$ surface layer portion and Ni component were reacted with each other by heat treatment at 1400° C. for 1 hour to form a $Ni_2TiO_4$ layer. The $Ni_2TiO_4$ layer was subjected to reduction treatment at 1000° C. for 10 minutes in a hydrogen atmosphere to obtain a catalyst material having Ni particles on the surface layer portion. The catalyst performance evaluation test on this material was performed.

Example 22

A catalyst material having Ni particles on the surface layer portion of Comparative Example 4 was further immersed in an aqueous solution of cerium nitrate and subjected to vacuum impregnation, and after drying the catalyst material, heat treatment was performed at 500° C. for 1 hour to form a $CeO_2$ layer. The catalyst performance evaluation test on this sample was performed.

The performance test results of the catalysts of Examples and Comparative Examples are collectively presented in Table 1.

Example 23

In Example 1, after the reductive precipitation treatment of the catalyst, an aqueous solution of cerium nitrate (Ce $(NO_3)_3.6H_2O$) and iron nitrate ($Fe(NO_3)_3.9H_2O$) were mixed at a molar ratio of 10:1, the mixed solution was subjected to impregnation and dried, and then heat treatment was performed at 500° C. for 1 hour to form a mixed layer of $Fe_2O_3$—$CeO_2$ on the surface of the catalyst. The catalyst performance evaluation test was performed using this sample. $Fe_2O_3$ was reduced in the reduction treatment before the test and the covered layer became the $CeO_2$ layer having Fe fine particles dispersed therein.

Example 24

In Example 1, after the reductive precipitation treatment of the catalyst, an aqueous solution of cerium nitrate (Ce $(NO_3)_3.6H_2O$) and cobalt nitrate ($Co(NO_3)_2.6H_2O$) were mixed at a molar ratio of 10:1, the mixed solution was subjected to impregnation and dried, and then heat treatment was performed at 500° C. for 1 hour to form a mixed layer of CoO—$CeO_2$ on the surface of the catalyst. The catalyst performance evaluation test was performed using this sample. CoO was reduced in the reduction treatment before the test and the covered layer became the $CeO_2$ layer having Co fine particles dispersed therein.

TABLE 1A

| | First metals | Second metals | Metal supported amount (wt %) | Base material | First oxide |
|---|---|---|---|---|---|
| Example 1 | Ni | — | 9.4 | $Al_2O_3$ | $CeO_2$ |
| Comparative Example 1 | Ni | — | 9.4 | $Al_2O_3$ | — |
| Example 2 | Ni | — | 9.4 | $Al_2O_3$ | $CeO_2$ |
| Example 3 | Ni | — | 16.2 | $Al_2O_3$ | $CeO_2$ |
| Example 4 | Ni | — | 9.4 | $Al_2O_3$ | $CeO_2$—$Sm_2O_3$ |
| Example 5 | Ni | — | 9.4 | $Al_2O_3$ | $CeO_2$—$Y_2O_3$ |
| Example 6 | Ni | — | 9.4 | $Al_2O_3$ | $CeO_2$—$Gd_2O_3$ |
| Example 7 | Ni | — | 9.4 | $Al_2O_3$ | $CeO_2$—$La_2O_3$ |
| Example 8 | Ni | — | 9.4 | $Al_2O_3$ | $CeO_2$—$La_2O_3$ |
| Example 9 | Ni | — | 9.4 | $Al_2O_3$ | $CeO_2$ |
| Example 10 | Ni | — | 9.4 | $Al_2O_3$ | $ZrO_2$ |
| Example 11 | Ni | — | 9.4 | $Al_2O_3$ | $ZrO_2$—$Sm_2O_3$ |
| Example 12 | Ni | — | 9.4 | $Al_2O_3$ | $ZrO_2$—$Y_2O_3$ |
| Example 13 | Ni | — | 9.4 | $Al_2O_3$ | $ZrO_2$—$Gd_2O_3$ |
| Example 14 | Ni | — | 9.4 | $Al_2O_3$ | $ZrO_2$—$La_2O_3$ |
| Example 15 | Ni | — | 9.4 | $Al_2O_3$ | $ZrO_2$ |
| Example 16 | Ni | — | 9.4 | $Al_2O_3$ | $CeO_2$—$ZrO_2$ |
| Example 17 | Ni | — | 9.4 | $Al_2O_3$ | $SiO_2$ |
| Example 18 | Ni | — | 9.4 | $Al_2O_3$ | $TiO_2$ |
| Comparative Example 2 | Ni | — | 9.4 | MgO | — |
| Example 19 | Ni | — | 9.4 | MgO | $CeO_2$ |
| Example 20 | Ni | — | 9.4 | MgO | $ZrO_2$ |
| Comparative Example 3 | Ni | — | 9.4 | $TiO_2$ | — |
| Example 21 | Ni | — | 9.4 | $TiO_2$ | $CeO_2$ |
| Comparative Example 4 | Ni | — | 9.4 | $SiO_2$ | — |
| Example 22 | Ni | — | 9.4 | $SiO_2$ | $CeO_2$ |
| Example 23 | Ni | Fe | Ni 8.4 Fe 0.8 | $Al_2O_3$ | $CeO_2$ |
| Example 24 | Ni | Co | Ni 8.4 Co 0.8 | $Al_2O_3$ | $CeO_2$ |

TABLE 1B

| | Test temperature (° C.) | | | |
|---|---|---|---|---|
| | 250 | 300 | 350 | 400 |
| Example 1 | 10.8 | 55.9 | 83.5 | 82.9 |
| Comparative Example 1 | 1.6 | 10.0 | 50.0 | 78.0 |
| Example 2 | 3.0 | 23.3 | 65.3 | 80.3 |
| Example 3 | 18.3 | 64.3 | 87.5 | 83.5 |

TABLE 1B-continued

| | Test temperature (° C.) | | | |
|---|---|---|---|---|
| | 250 | 300 | 350 | 400 |
| Example 4 | 15.4 | 61.5 | 85.1 | 83.3 |
| Example 5 | 13.9 | 60.3 | 83.7 | 84.8 |
| Example 6 | 29.4 | 69.7 | 88.8 | 83.0 |
| Example 7 | 37.5 | 80.5 | 90.8 | 84.5 |
| Example 8 | 45.2 | 85.7 | 91.0 | 85.0 |
| Example 9 | 1.2 | 19.4 | 64.1 | 80.2 |
| Example 10 | 12.0 | 49.9 | 78.0 | 82.3 |
| Example 11 | 19.4 | 69.8 | 85.2 | 84.7 |
| Example 12 | 20.3 | 64.8 | 83.1 | 82.5 |
| Example 13 | 27.3 | 69.7 | 85.5 | 84.3 |
| Example 14 | 36.4 | 76.0 | 88.7 | 83.8 |
| Example 15 | 9.1 | 44.0 | 79.1 | 82.0 |
| Example 16 | 19.0 | 65.4 | 85.6 | 84.5 |
| Example 17 | 4.1 | 21.5 | 60.8 | 78.4 |
| Example 18 | 5.2 | 44.3 | 76.6 | 80.6 |
| Comparative Example 2 | 0.0 | 6.7 | 28.9 | 61.6 |
| Example 19 | 4.2 | 28.8 | 67.4 | 80.8 |
| Example 20 | 3.5 | 25.5 | 63.6 | 79.6 |
| Comparative Example 3 | 0.0 | 6.8 | 30.8 | 70.0 |
| Example 21 | 5.1 | 33.3 | 73.0 | 81.6 |
| Comparative Example 4 | 0.0 | 6.5 | 28.3 | 60.2 |
| Example 22 | 4.7 | 28.8 | 68.2 | 80.9 |
| Example 23 | 20.2 | 73.0 | 88.2 | 83.5 |
| Example 24 | 13.2 | 61.8 | 83.5 | 83.1 |

As clearly seen from Tables (Table 1A and Table 1B), it was found that the first metals and the base material and the first oxide, which are integrated with the first metals, were allowed to simultaneously exist and thus the methane yield was improved.

Particularly, in a case where the oxide layer (the first oxide) was formed after reduction treatment, including Example 1, it was found that the covered oxide was formed without a change in composition thereof and methane was generated at a higher yield. In addition, although not shown in Table 1, it was clear that the generation of CO, which was observed in Comparative Example 1, was almost not observed and $CO_2$ was rapidly reduced to $CH_4$.

Further, in the case of the $Al_2O_3$ base material, the crystalline phase was changed from a γ type of low-temperature type to an α type at the stage of forming the $NiAl_2O_4$ layer by sintering. According to this, it was found that the specific area was decreased; however, when pores having a size of about 1 μm were introduced as described in Example 3, the metal component could be impregnated and precipitated in a wider range, and the first metals formed in the deep portion could also contribute to reaction so that the activity was further improved.

Figure 7:
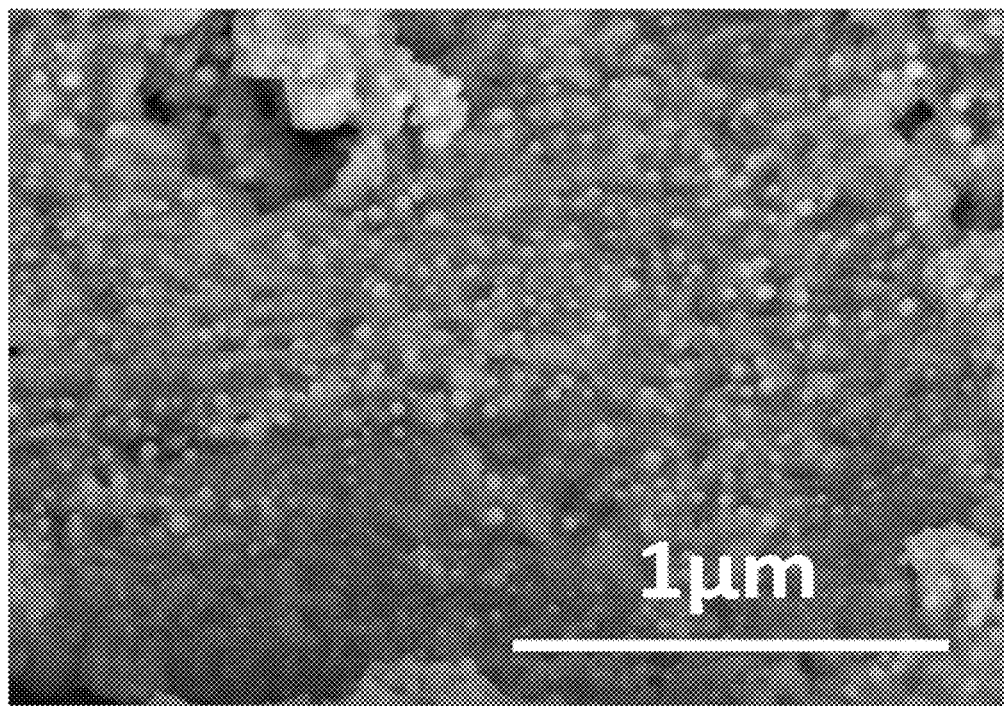
FIG. 7 is a photographed image of the microstructure observation of the catalyst according to the embodiment.

FIG. 7 shows a photographed image of the typical microstructure of the catalyst according to the embodiment. FIG. 7 is obtained by observing the structure of the surface portion of the catalyst prepared in Example 2 and is a reflected electron image photographed in such a manner that an acceleration voltage was set to slightly high and thus the structure of the inner portion of the sample was further captured. In the drawing, particulate white spots are Ni particles of metal. The size of Ni particles was about 30 to 60 nm and was sufficiently larger than the size of Ni particles of a general catalyst. In this way, the Ni particles each independently exist on the surface portion of the catalyst and have a structure in which the particles are highly dispersed. This structure is considered to improve durability. In addition, a Ce-containing layer was formed on the surface portion of this particle and in the vicinity thereof. In this case, $CeO_2$ subjected to coating treatment at the time of reduction treatment was reacted with $Al_2O_3$ of the base material to form a $CeAlO_3$ layer. From a result of catalyst performance test, activity is improved as compared with the case of having no layer. That is, it was found that even when the oxide layer and the base material as described above were reacted with each other to form a compound, there is no problem in improvement of catalyst activity and the effect is achieved.

The sample described in Example 1 in which the oxide layer was formed after the other treatments were performed was also observed with a SEM, but the structure thereof was the same phase as illustrated in FIG. 1B.

Regarding the content of Ni, the test was also performed on a sample having a Ni supported amount of less than 5 wt %, but although there was a $CeO_2$ layer, the catalyst for changing the dissociated $CO_2$ into methane was not sufficient and the performance thereof was deteriorated. In contrast, when the Ni supported amount was increased, the activity was improved, but the activity almost reached to the peak in an area having a Ni supported amount of more than 25% by mass. When the supported amount increases, there is a concern of deterioration in performance caused by combining or growth of Ni particles while in use. For this reason, the supported amount of the first metals is preferably set to 20% by mass or less. Further, regarding the first oxide, in addition to $CeO_2$, the same effect was also recognized in $SiO_2$, $TiO_2$, and $ZrO_2$. Regarding to material that is coated with rare-earth oxide and is heat-treated at the same time, solid-solubilization into $CeO_2$ and $ZrO_2$ and improvement in catalyst performance at low temperature were confirmed.

Furthermore, the catalyst performance test was performed on a sample in which a component such as Co, Fe, or Cu was added in advance instead of Ni and the component was precipitated by reduction at the same time of precipitation of Ni. As a result of the test, in all cases, the methane yield was lowered as compared with a case where Ni was added alone. In addition, remaining CO, which is generated when $CO_2$ is not completely turned into $CH_4$, was observed. In contrast, in the catalysts using Co particles or Fe particles together with Ni particles as the first metals, the methane yield is improved. When the oxide layer such as $CeO_2$ was provided in the catalysts, it was confirmed that the catalyst activity is improved.

The performance evaluation results of the catalysts in which Fe and Co were added as the second metals (Example 23 and Example 24) are presented in Table 1. The methane yield at the low temperature region is improved as compared with the case of using only the first metals. On the other hand, in another test, the system in which Fe and Co are simply supported on $Al_2O_3$ did almost not exhibit the catalyst activity. The reason for this is found that this catalyst activity is a specific phenomenon occurring when the second metals are combined with the first metals. It is considered that fine particles of Fe and Co play a role of assisting the catalyst performance of Ni, that is, act as a cocatalyst. Further, the catalysts of Examples were observed with TEM-EDX to confirm that the first metals, the first oxide, and the second metals exist on the surface of the base material in the fine pores. In addition, some of the fine pores were connected with each other and unevenness having a size of 5 μm or more and 20 μm or less was confirmed on the outer surface of the catalyst. A mapping result of EDX in which it is considered that some of the first metals have interfaces with the first oxide or the first oxide and the second metals as well as the base material was obtained. It is considered that low-temperature activity is improved by improving catalyst characteristics when a lot of catalyst activity points exist in the fine pores.

It was confirmed that the catalysts of Examples are excellent in activity at low temperature without use of a noble metal in a catalytic metal (metal particles). In addition, since the metal particles are configured to be held by both the base material and the oxide layer, the metal particles are less likely to drop off even in high-temperature environment or long-term use. For this point of view, the catalysts of Examples (embodiments) are catalysts that are excellent in terms of all aspects of inexpensiveness, high low-temperature activity, and durability, which are required for practical use. In addition, although methane is generated using the catalyst in Examples, similarly, methanol is generated by changing a raw material from carbon dioxide to carbon monoxide. Further, these catalysts are expected to exhibit higher performance even under increased pressure generally used for increasing the reaction rate.

In the specification, some elements are described only by chemical symbols.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A fuel synthesis catalyst for hydrogenating a gas containing at least one selected from the group consisting of; carbon dioxide and carbon monoxide, the catalyst comprising:
    a base material containing at least one oxide selected from the group consisting of; $Al_2O_3$, MgO, $TiO_2$, and $SiO_2$;
    first metals containing at least one metal selected from the group consisting of; Ni, Co, Fe, and Cu and brought into contact with the base material; and
    a first oxide containing at least one selected from the group consisting of; $CeO_2$, $ZrO_2$, $TiO_2$, and $SiO_2$ and having an interface with each of the first metals and the base material, wherein
    the first metals exist on an outer surface of the base material, and on a surface of the base material in fine pores having opening ends on the outer surface of the base material and inside the base material,
    the first metals and the first oxide exist in the fine pores,
    the first metals have interfaces with the base material in the fine pores, and
    the first metals exist inside the base material.

2. The catalyst according to claim 1, wherein the first oxide has an interface with the first metals in the fine pores, and
    the first oxide partially or entirely covers the outer surface of the base material.

3. The catalyst according to claim 1, wherein a content of the first metals is 5% by mass or more and 20% by mass or less.

4. The catalyst according to claim 1, wherein an average particle diameter of the first metals is 2 nm or more and 200 nm or less, and
    an average particle diameter of the fuel synthesis catalyst is 2 mm or more and 10 mm or less.

5. The catalyst according to claim 1, wherein the first oxide contains a solid-solubilized product with a second oxide containing a rare-earth oxide.

6. The catalyst according to claim 5, wherein the rare-earth oxide contains at least one element selected from the group consisting of; La, Sm, Gd, and Y.

7. The catalyst according to claim 5, wherein the rare-earth oxide solid-solubilized in the first oxide is contained in 10 mol % or more and 60 mol % or less of the first oxide.

8. The catalyst according to claim 1, being a hydrocarbon fuel synthesis catalyst or an alcohol fuel synthesis catalyst.

9. A fuel synthesis system comprising:
    a reaction column provided with the fuel synthesis catalyst according to claim 1;
    a first raw material supply line supplying one or both of carbon dioxide and carbon monoxide to the reaction column;
    a second raw material supply line supplying hydrogen to the reaction column; and
    a recovery unit recovering a fuel generated by reacting one or both of the carbon dioxide and the carbon monoxide with the hydrogen using the catalyst in the reaction column.

10. The system according to claim 9, wherein a temperature of reaction of the carbon dioxide or carbon monoxide with the hydrogen using the catalyst is 250° C. or higher but 400° C. or lower.

11. A fuel synthesis catalyst for hydrogenating a gas containing at least one selected from the group consisting of; carbon dioxide and carbon monoxide, the catalyst comprising:
    a base material containing at least one oxide selected from the group consisting of; $Al_2O_3$, MgO, $TiO_2$, and $SiO_2$;
    first metals containing at least one metal selected from the group consisting of; Ni, Co, Fe, and Cu and brought into contact with the base material;
    a first oxide containing at least one selected from the group consisting of; $CeO_2$, $ZrO_2$, $TiO_2$, and $SiO_2$ and having an interface with each of the first metals and the base material; and
    second metals containing a metal different from a metal included in the first metals among the at least one metal selected from the group consisting of; Ni, Co, Fe, and Cu, wherein
    the first metals exist on an outer surface of the base material, and on a surface of the base material in fine pores having opening ends on the outer surface of the base material and inside the base material,
    the first metals, the first oxide, and the second metals exist in the fine pores,
    the first metals have interfaces with the base material in the fine pores,
    the second metals have interfaces with the first metals in the fine pores, and
    the first metals exist inside the base material.

12. The catalyst according to claim 11, wherein a particle diameter of the first metals in which a cumulative volume curve in particle size distribution is 16% is larger than a particle diameter of the second metals in which a cumulative volume curve in particle size distribution is 84%.

13. The catalyst according to claim 11, wherein a proportion of the first metals and the second metals contained in the fuel synthesis catalyst is 5% by mass or more and 40% by mass or less.

14. The catalyst according to claim 11, wherein the first oxide has an interface with the first metals in the fine pores, and the first oxide partially or entirely covers the outer surface of the base material.

15. The catalyst according to claim 11, wherein an average particle diameter of the first metals is 2 nm or more and 200 nm or less,
an average particle diameter of the second metals is 2 nm or more and 100 nm or less, and
an average particle diameter of the fuel synthesis catalyst is 2 mm or more and 10 mm or less.

16. The catalyst according to claim 11, wherein the first oxide contains a solid-solubilized product with a second oxide containing a rare-earth oxide.

17. The catalyst according to claim 16, wherein the rare-earth oxide contains at least one element selected from the group consisting of; La, Sm, Gd, and Y.

18. The catalyst according to claim 16, wherein the rare-earth oxide solid-solubilized in the first oxide is contained in 10 mol % or more and 60 mol % or less of the first oxide.

19. A fuel synthesis system comprising:
a reaction column provided with the fuel synthesis catalyst according to claim 11;
a first raw material supply line supplying one or both of carbon dioxide and carbon monoxide to the reaction column;
a second raw material supply line supplying hydrogen to the reaction column; and
a recovery unit recovering a fuel generated by reacting one or both of the carbon dioxide and the carbon monoxide with the hydrogen using the catalyst in the reaction column.

20. The system according to claim 19, wherein a temperature of reaction of the carbon dioxide or carbon monoxide with the hydrogen using the catalyst is 250° C. or higher but 400° C. or lower.

* * * * *